United States Patent

Walele et al.

Patent Number: 6,069,262
Date of Patent: May 30, 2000

[54] FATTY ACID ESTERS OF HYDROXYALKYL SULFONATE SALTS AND PROCESS FOR PRODUCING SAME

[75] Inventors: Ismail I. Walele, Saddle Brook; Samad A. Syed, Paramus, both of N.J.

[73] Assignee: Finetex, Inc., Elmwood Park, N.J.

[21] Appl. No.: 08/944,812

[22] Filed: Oct. 6, 1997

[51] Int. Cl.[7] ................................................ C07C 303/00
[52] U.S. Cl. ................................................ 554/92; 554/98
[58] Field of Search .................................... 584/92, 98

[56] References Cited

U.S. PATENT DOCUMENTS

| | | |
|---|---|---|
| 1,881,172 | 10/1932 | Daimler et al. |
| 2,303,582 | 12/1942 | Russell et al. |
| 2,307,953 | 1/1943 | Potter. |
| 2,316,719 | 4/1943 | Russell. |
| 2,328,931 | 9/1943 | Steik. |
| 2,635,103 | 4/1953 | Molteni et al. |
| 2,806,044 | 9/1957 | Weil et al. |
| 2,821,535 | 1/1958 | Britton et al. |
| 2,857,370 | 10/1958 | Sundberg. |
| 2,863,887 | 12/1958 | Becher. |
| 2,898,352 | 8/1959 | Schenck. |
| 2,923,724 | 2/1960 | Anderson et al. |
| 3,004,049 | 10/1961 | Schenck. |
| 3,029,264 | 4/1962 | van Alphen et al. |
| 3,150,156 | 9/1964 | Lamberti. |
| 3,151,156 | 9/1964 | Marten et al. |
| 3,167,570 | 1/1965 | Bohunek. |
| 3,320,292 | 5/1967 | Cahn et al. |
| 3,383,396 | 5/1968 | Cahn et al. |
| 3,394,155 | 7/1968 | Cahn et al. |
| 3,420,857 | 1/1969 | Holland et al. |
| 3,420,858 | 1/1969 | McCrimlisk. |
| 3,429,136 | 2/1969 | Holt et al. |
| 3,745,181 | 7/1973 | Wrigley et al. |
| 3,880,897 | 4/1975 | Landy. |
| 3,997,576 | 12/1976 | Oghoshi et al. |
| 4,092,259 | 5/1978 | Prince. |
| 4,096,082 | 6/1978 | Prince. |
| 4,100,097 | 7/1978 | O'Roark. |
| 4,151,105 | 4/1979 | O'Roark. |
| 4,352,759 | 10/1982 | Schwarte. |
| 4,369,144 | 1/1983 | Lamberti et al. |
| 4,405,526 | 9/1983 | Lamberti. |
| 4,476,055 | 10/1984 | Du Vernet. |
| 4,515,721 | 5/1985 | Login et al. |
| 4,536,338 | 8/1985 | Urban et al. |
| 4,537,724 | 8/1985 | McKinnie et al. |
| 5,041,233 | 8/1991 | Kutny et al. |
| 5,069,828 | 12/1991 | Dumas et al. |
| 5,121,611 | 6/1992 | Broderdorf et al. |
| 5,300,665 | 4/1994 | Tracy. |
| 5,384,421 | 1/1995 | Day et al. ................ 554/92 |
| 5,393,466 | 2/1995 | Ilardi et al. |
| 5,434,276 | 7/1995 | Walele et al. |
| 5,496,959 | 3/1996 | Day. |
| 5,523,432 | 6/1996 | Raths et al. |

OTHER PUBLICATIONS

Publication—Surface Active Agents, etc. Nov. 1971.

*Primary Examiner*—Deborah D. Carr
*Attorney, Agent, or Firm*—Weingram & Association, P.C.

[57] ABSTRACT

Compositions of matter comprising fatty acid esters of hydroxyalkyl sulfonate salts, in particular sodium cocoyl isethionate (SCI) and process for preparing same. The esters are useful for personal care cleansing products, such as bar and liquid soaps, skin and hair care products.

36 Claims, 1 Drawing Sheet

FATTY ACID ESTERS OF HYDROXYALKYL SULFONATE SALTS AND PROCESS FOR PRODUCING SAME

BACKGROUND OF THE INVENTION

1. Field of the Invention

This invention relates generally to improved ester compositions, and more particularly to fatty acid esters of hydroxyalkyl sulfonate salts, referred to in the industry as sodium cocoyl isethionate (SCI). The esters are useful for personal care cleansing products, such as bar and liquid soaps, skin and hair care products.

2. Description of the Related Art

Esters and acids are known for a variety of different applications for cosmetic, pharmaceutical and medicinal purposes.

For example, U.S. Pat. No. 2,806,044 to WEIL et al. discloses detergent compositions prepared by the direct esterification of an α-sulfonated fatty acid with hydroxyalkanesulfonate. Since the α-sulfonated acid reagent is strongly acidic, no catalyst is required for production of the esters. Esterification is conducted under conditions such that water produced is removed from the reaction as fast as formed. Removal of the water may be done by use of an inert solvent that distills azeotropically with water.

U.S. Pat. No. 2,923,724 to ANDERSON et al. discloses a process for preparing ester type anionic surface active agents wherein a critical feature of the process is the presence of a phosphorous containing compound as a catalyst (Col. 2, lines 12–15). Anderson et al. compares the reactive components without a catalyst (Example 1) with the preferred process in which a catalyst is employed (Example 2). In Example 1, coconut oil fatty acid heated to 200° C. was mixed with sodium isethionate. The mixture was heated to 210° C. under an inert atmosphere of carbon dioxide. The reaction contained 20% of active material after two hours; the reaction rate was approximately 34% at the end of 3.5 hours. Catalysts are used in the process to improve reaction rates.

U.S. Pat. No. 5,523,432 to RATHS et al. discloses a process for the production of quaternary ammonium salts of fatty acid hydroxyalkanesulfonic acids, wherein the process is carried out at considerably lower temperatures than known process (at temperatures of from about 60° C. to about 120° C.) and without a catalyst. Water of solution and water of reaction are removed from the reaction mixture by distillation. Raths et al. points out that the advantage of carrying out the reaction without a catalyst is that there is thus no need to remove the catalyst from the reaction product and no catalyst residues are present in the reaction product. Catalysts also contribute to discoloration of the products. Raths et al. does not teach or suggest producing fatty acid esters using sodium hydroxysulfonate, which has a high melting point. Rather, Raths et al. discloses production of ammonium or amine salts using hydroxysulfonic acid, which has a lower melting point, and using solvents for conversion into amine salts.

U.S. Pat. No. 4,515,721 to LOGIN et al. discloses a process for preparing fatty acid esters of hydroxyalkyl sulfonic acid salts (i.e., hydroxyalkyl sulfonates) by heating an excess of the fatty acids with the hydroxyalkyl sulfonate, i.e., sodium isethionate, to a temperature of 200° C. to 250° C. until the water of condensation is removed. The hot crude ester is then quenched by immersion in an excess of cooled liquid such as an alcohol solvent, in which the ester product is substantially insoluble but in which unreacted, excess fatty acids are soluble. The resulting slurry is filtered to separate the relatively pure ester from the quenching liquid containing dissolved free fatty acid. The method of this patent recites a temperature range of 200° C. to 250° C., but all of the examples appear to be run at 250° C.

U.S. Pat. No. 5,300,665 to TRACY et al. discloses preparation of fatty acid esters of hydroxyalkylsulfonates (i.e., sodium cocyl isethionate) by heating an excess of the fatty acids with the sulfonate in the presence of a reaction promoter (catalyst) at a temperature between about 200° C. to 250° C. in a substantially oxygen-free atmosphere until the water of condensation is removed. The excess fatty acid is removed by distillation and the isolated fatty acid ester is cooled to minimize decomposition and color degradation.

U.S. Pat. No. 3,420,857 to HOLLAND et al. and U.S. Pat. No. 3,420,858 to McCRIMLISK disclose methods for preparing fatty esters of hydroxysulfonates to obtain products which have reduced amounts of esters of higher molecular weight fatty acids and unreacted lower molecular weight fatty acids. The methods comprise continuously supplying to the reaction vessel, fatty acid reactants of a composition corresponding to fatty acids volatilized during the course of the reaction (in order to reduce the proportion of esters of relatively higher molecular weight fatty acids) and utilizing an improved stripping process to reduce the lower molecular weight fatty acid content. The method includes heating a mixture of an hydroxyalkylsulfonate and fatty acids to a temperature between about 390° F. to 500° F. (about 199° C. to 260° C.) The examples are run at temperatures of at least 450° F. (about 232° C.). The patents note that temperatures below 232° C. significantly reduce reaction rates. While it is preferred to employ a reaction promoter to boost yields of the desired product, promoters are optional. In the absence of promoters, higher temperatures, such as up to about 500° F., (about 260° C.), are usually necessary to avoid premature cessation of the reaction. (Holland, Col. 2, lines 40–42; McCrimlisk, col. 2., lines 15–23). Neither McCrimlisk nor Holland teach or suggest a process in which there is none to negligible change in the molecular weight distribution of the SCI product.

U.S. Pat. No. 3,429,16 to HOLT et al. discloses a method for making esters of hydroxysulfonates in which the hot hydroxy-sulfonate esters are cooled from temperatures of about 350° F. to 500° F. (about 177° C. to 260° C.) to a temperature below about 330° F. (about 165.6° C.). At this point the reaction is quenched by injecting cold water. Reaction promoters are optionally provided to achieve acceptable conversion levels. In the presence of such reaction promoters, the reaction may be carried out at temperatures of 390° F. to 465° F. In the absence of such promoters, higher temperatures, such as up to about 500° F. (about 260° C.) are usually necessary to avoid premature cessation of the reaction.

U.S. Pat. No. 3,394,155 to CAHN et al. discloses a method for preparing esters of predominantly coco fatty acid and a hydroxy sulfonate by direct esterification which minimizes the residues of unreacted fatty acids of $C_8$–$C_{12}$ carbon chain lengths. This is achieved by adding the fatty acid reactant in two steps. First, coco fatty acids containing substantial quantities of the $C_8$–$C_{12}$ fatty acids are added in sufficient quantities to provide the desired proportion of coco esters in the final product, but insufficient to completely consume the hydroxy sulfonate. In the second step sufficient additional fatty acid is added to provide a high conversion of the hydroxy sulfonate, the additional fatty acid, however, containing substantially lower proportions of the $C_8$–$C_{12}$ fatty acids. In the absence of a reaction promoter, a temperature of about 200° C. to about 250° C. is required. If a reaction promoter is employed, the maximum reaction temperature need not exceed about 240° C.

U.S. Pat. No. 3,320,292 to CAHN et al. discloses preparation of sulfonated fatty acid ester surface-active agents. Examples 3 and 4 show that when coconut oil fatty acids are mixed with sodium isethionate in the presence of a catalyst of zinc oxide or zinc soap, esterification proceeds at lower temperatures (about 230° C.) and shorter times (1 to 1.5 hours) with higher yields (90%–97%). In Example 1, when no catalyst is used, esterification proceeds at a temperature of about 240° C.–251° C. and the reaction is substantially complete in approximately 2 hours, with conversion percentages of between 87%–89%.

U.S. Pat. No. 3,092,264 to VAN ALPHEN et al. discloses preparation of a mixture of fatty acyl-oxyalkane sulphonates. In discussing the prior art in col. 1, lines 14–30, the '264 patent notes that merely heating together a fatty acid and a hydroxyalkane sulphonate such as an isethionate (without a promoter) has several disadvantages. Excessive foaming occurs necessitating the use of very large reaction vessels, vigorous stirring is required to ensure adequate mixing, reduced pressure must be maintained throughout the reaction, and the products are typically discolored.

U.S. Pat. No. 4,536,338 to URBAN et al. discloses a method for preparing fatty acid isethionate soaps through direct esterification wherein the catalyst is quenched by an alkaline compound at the end of the esterification and the traditional stripping step to remove excess $C_5$–$C_{12}$ fatty acids following esterification may be eliminated. Urban et al. further teach that the choice of catalyst effects chain length distribution of the isethionate ester product.

U.S. Pat. No. 2,821,531 to BRITTON et al. discloses a process for making 2-sulfoethyl esters of fatty acids wherein a mixture of a salt of isethionic acid and a fatty acid chloride, i.e. an acylchloride of a fatty acid such as fatty acids derived from coconut oil, are admixed at temperatures between 135° C. and 170° C. during which hydrogen chloride is usually withdrawn from the reaction at about the rate it is formed. The process is employed to react salts of isethionic acid with fatty acid chlorides to yield the corresponding isethionate ester.

U.S. Pat. No. 3,150,156 to LAMBERTI discloses a catalytic process for preparing N-acyl taurates, wherein when a catalyst is not used, unsatisfactory results are obtained (see TABLE I).

U.S. Pat. No. 4,405,526 to LAMBERTI et al. discloses a process for producing esterified fatty acid isethionate by reacting a fatty acid with an alkali metal isethionate in the presence of a catalyst comprising a mixture of ZnO and an organic sulfonic acid and heating at about 200° C. to about 255° C.

U.S. Pat. No. 5,384,421 to DAY et al. discloses a process for making sodium acylisethionates, wherein there is direct esterification of a fatty acid with one or more salts of a selected hydroxyalkanesulfonic acid in the presence of a catalyst. The process makes fatty acid esters of hydroxyalkyl sulfonates and may be used at temperatures below 200° C. in the presence of paraffin wax to lower the viscosity so that complete condensation can be achieved. There is hydrolysis of the ester. Stearic acid and NaOH are added to the cooled reaction mass. Water is mixed with the cooled reaction mass to form a pumpable fluid.

U.S. Pat. No. 5,434,276 to WALELE et al. discloses a process for making N-acyl taurides. An alkali metal borohydride acts as a catalyst in the reaction, although such may act as a reducing agent to promote the reaction.

However, among the foregoing patents, none disclose or suggest a process for the production of fatty acid esters of hydroxyalkyl sulfonate salts, wherein the fatty acids are maintained in a closed system and returned to the reactor vessel, and water is continuously removed without requiring a catalyst for the process or alkalies to quench the catalyst. The reaction is maintained fluid throughout. Neither are any of the foregoing patents directed to compositions of fatty acid esters of hydroxyalkyl sulfonate salts having superior properties, superior color, odor and activity integrity, with none or negligible change in the molecular weight distribution and with high conversion of sodium isethionate.

OBJECTS AND SUMMARY OF THE INVENTION

It is an object of this invention to provide novel fatty acid esters of hydroxyalkyl sulfonate salts having unique properties which make them uniquely suitable for use in cosmetics, skin care products, personal care products such as body washes, cleansers, creams, lotions, shampoos, and other topical applications and products.

Another object of the invention is to produce fatty acid esters of hydroxyalkyl sulfonate salts without the use of catalysts, promoters, expediters or accelerators.

It is a further object of this invention to provide fatty acid esters of hydroxyalkyl sulfonate salts having superior properties, namely high color and odor integrity, with none or negligible change in the molecular weight distribution.

Yet another object of the invention is the provision of fatty acid esters of hydroxyalkyl sulfonate salts of defined molecular weight that is equal to or nearly equal to the derived molecular weight of the starting fatty acids and hydroxyalkyl sulfonate.

Yet a further object of the invention is the production of reduced alkalinity fatty acid esters of hydroxyalkyl sulfonate salts with none or negligible amounts of unaccounted impurities or unnecessary, unreacted reactants.

Yet another object of the invention is to produce very high yields of soap-free sodium cocyl isethionate of defined molecular weight with high conversion of sodium isethionate.

These and other objects are obtained by reacting an excess of fatty acids and hydroxyalkyl sulfonate. The compositions provided include many unique effects as compared to commercially available SCI products.

DETAILED DESCRIPTION OF THE INVENTION

Figure 1:
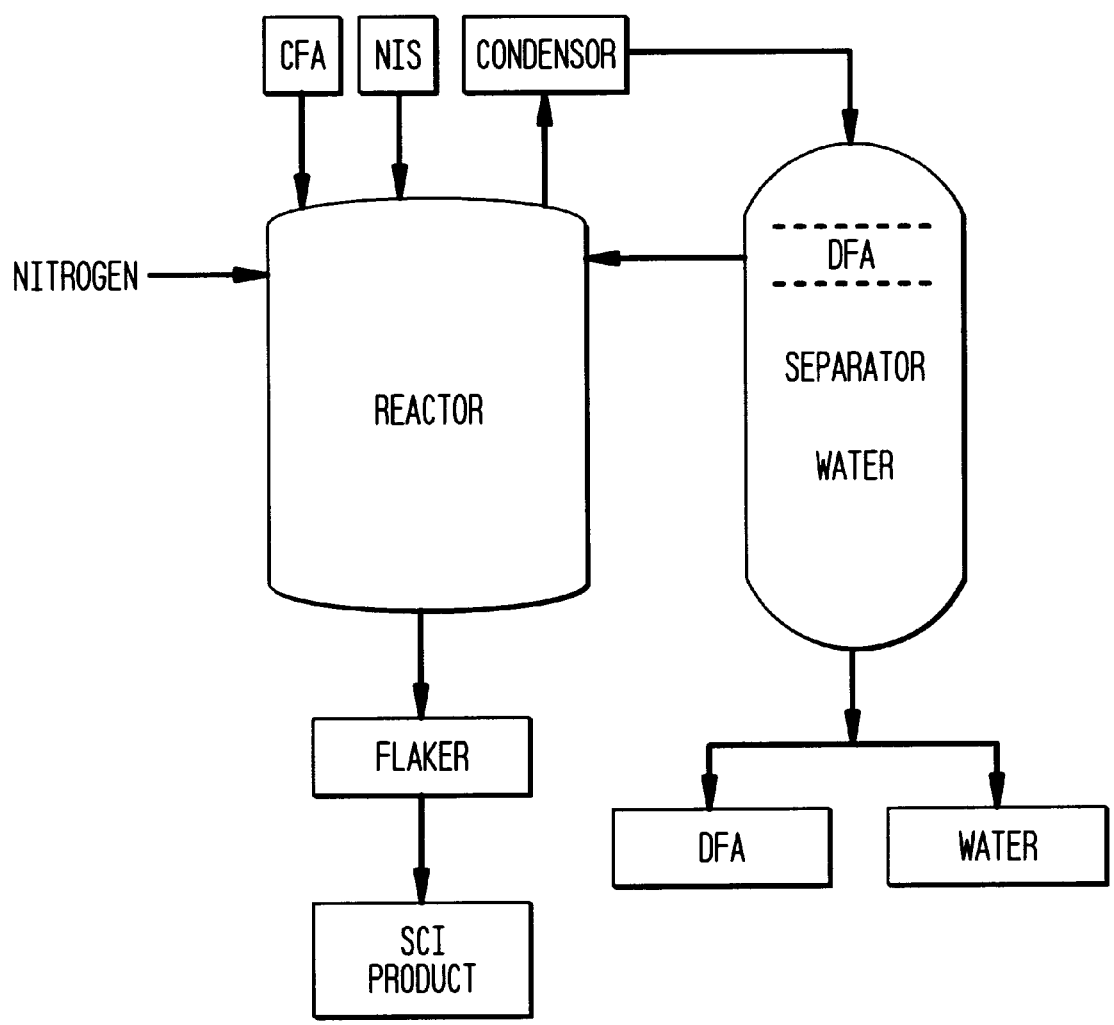

For a further understanding of the process of the invention, reference may be had to the attached FIG. 1 which represents a simplified flow diagram for the synthesis of SCI product of the invention.

Fatty acid esters of hydroxyalkyl sulfonate salts are known in the industry as sodium cocoyl isethionate (SCI), CAS #61789-32-0, IUPAC name: Fatty Acids, coco, 2-sulfoethyl esters, sodium salts.

Fatty acids to be employed in the process may contain from 8 to 18 carbon atoms, although higher fatty acids such as C20–C24 fatty acids may be employed. Fatty acids derived from coconut oil are preferred. Specifically, fatty acids including but not limited to the following coco fatty acids, may be used: coco fatty acids (C8–C18, C18 unsaturated); coco fatty acids (stripped to remove C8/C10 acids); stripped hydrogenated coco fatty acids (absence of C8/C10 acids); hydrogenated coco fatty acids (C8–C18 range); individual C12 through C18 fatty acids (C18 includes saturated/unsaturated). Any combination of C8 through C18 fatty acids or C18 unsaturated fatty acid may be used.

EMERY® 626 (Henkel Corp., Cincinnati, Ohio) is the most preferred coconut fatty acid and has the following typical specifications: titer of 23° C.–26° C., iodine value of 1.0 max. cg./g., color of Gardner 1963 max. 1 and 85/–% Trans 440/550 nm., min., acid value of 270–276 mg. KOH/gm. and an average molecular weight of 208. EMERY® 626 has a typical composition determined by GLC analysis, AOCS Ca 1–62, of:

%

7 caprylic acid;

6 capric acid;

51 lauric acid;

18 myristic acid;

10 palmitic acid;

7 stearic acid; and 1 oleic acid

Water-soluble sodium isethionate (abbreviated herein as NIS) is a hydroxyethane sulfonic acid sodium salt of the formula HO—CH$_2$—CH$_2$—SO$_3$—NA. It is also known as sodium hydroxyethane sulfonate and is available from Witco Corporation, Perth Amboy, N.J., and Hoechest-Celanese Corporation, Pasadena, Tex. The sodium isethionate used in the process of the invention should have a maximum alkalinity of 1.5 mgms KOH/gm, and preferably an alkalinity between 0.2 and 0.7 mgms KOH/gm, and most preferably an alkalinity<0.5 mgms KOH/gm. The sodium isethionate should have a maximum acidity of 1.0 mgms KOH/gm, preferably an acidity<0.5 mgms KOH/gm, and most preferably an acidity<0.2 mgms KOH/gm.

During the reaction, alkalinity is not introduced by way of addition of alkaline catalysts or alkalies nor is it increased or reduced by any additions. Neither is acidity introduced, increased or reduced by way of additions of acidic catalysts/acids. NIS is used on an "as is" basis or in its dry form, without addition of organic or inorganic acids or alkalies, acidic or alkaline catalysts, metal salts, metal hydroxides, sulfonic ions or other sulfonic acid groups in the initial charge other than fatty acids and the salt of isethionic acid to act as reaction promoters or accelerators.

In the absence of a catalyst there is no need to quench or to remove the catalyst, there are no catalyst residues so there is minimal change in the molecular weight distribution of the product, there is no discoloration, the product has improved stability and solubility and processing time is decreased. A non-catalyzed process can advantageously proceed beyond the optimum time without resulting in deterioration of the product. Additionally, in a closed system, there is no need to selectively add higher molecular weight acids to the reaction to achieve fluidity of the reaction mass.

Fatty acids are mixed with a 2-hydroxyalkyl sulfonic acid salt of formula

HOR$^1$SO$_3$X wherein R$^1$ is a saturated or unsaturated straight chain C2–C4 hydrocarbyl group selected from the group consisting of ethylene, propylene and butylene; and X is selected from the group consisting of sodium, potassium, lithium, ammonium, calcium, magnesium, barium, amines, and triethanol amines.

Other salts of isethionic acid may be employed as starting materials, so long as the alkalinity and acidity values of the sulfonate is within the range set forth above. For instance, other alkali and alkaline earth metal salts of isethionic acid such as ammonium isethionate, potassium isethionate, lithium isethionate, calcium isethionate, magnesium isethionate or barium isethionate may be used. Hydroxyalkyl sulfonate may be in a different salt form, such as, for example, ammonium, amines, triethanol amines, etc. Other hydroxyalkane sulfonates such as hydroxypropane sulfonate salts, for instance sodium, potassium, ammonium salts, etc., may also be used. As the preferred salt of isethionic acid is sodium isethionate, NIS, that is the compound which will be used in the following description and examples.

In a specific embodiment, and by way of illustration, this invention contemplates the production of sodium cocoyl isethionate (SCI) in accordance with the following equation:

fatty acid+sodium isethionate (NIS)→sodium cocoyl isethionate

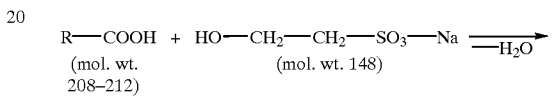
(mol. wt. 208–212)   (mol. wt. 148)

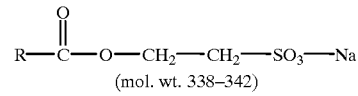
(mol. wt. 338–342)

wherein R is a fatty acid containing from 8 to 18 carbon atoms, although higher fatty acids such as C20–C24 fatty acids may be employed. Fatty acids derived from coconut oil, as described above, are preferred.

In the following discussion, the term "coco fatty acid" is used to refer to the coconut fatty acid used in the initial charge; by "free fatty acid" herein is meant the unreacted fatty acid in the reaction mass in process; by "distilled fatty acid" herein is meant the fatty acid returned during the reaction.

The starting materials are usually employed in stoichiometric proportions, but may be employed in amounts corresponding to from 1.0 mole of NIS to 1.5 moles of coco fatty acids, preferably from 1 mole of NIS to 1.4 moles of coco fatty acids, and most preferably from 1.0 mole of NIS to 1.3 moles of coco fatty acids employed, but can go as low as 1.0 mole of NIS to 1.2–1.25 moles of coco fatty acids with excellent results. It is preferred to use an excess of fatty acids in the reaction since the use of greater than stoichiometric quantities of fatty acids also serves to drive the reaction to completion. The reaction may be carried out batchwise or in a continuous manner. A batch process is preferred.

Fatty acid esters of hydroxyalkyl sulfonates are prepared by mixing together and heating an excess of fatty acids with the sulfonate in a suitable reaction vessel until water of condensation is nearly completely removed. The azeotroped water is continuously separated off and removed. The azeotroped fatty acids which are insoluble in water are concurrently returned to the reaction vessel, for full conversion into active surfactant of the invention. The free fatty acids are then distilled off, under reduced pressure, to achieve a high activity product of desired specifications.

More specifically, coco fatty acids and a 50–58% solution of sodium isethionate (NIS) are mixed together and heated in a reactor vessel of appropriate size, preferably with agitation, at atmospheric pressure, to a temperature in the range of 200° C. to 250° C., more preferably at about 220° C. to 250° C., and most preferably at about 240° C. The reactants are brought together and maintained under a substantially dry, inert atmosphere of nitrogen. Once the desired temperature range is reached, the reaction is allowed to continue toward completion.

Water which occurs during the reaction is continuously removed. Specifically, water evolved by the reaction together with steam distilled fatty acids begin to distill from the reactor. The vapors are condensed in a condenser. The water-fatty acid condensate is collected in a separator from which the distillate fatty acid is recovered for continuous return to the vessel. Residual water of dilution from sodium isethionate and the water of reaction is removed while the distillate fatty acids that escape the reaction mass are returned to the reaction mass. The distillate fatty acids in the separator are kept at a level above the reactor so that they may be easily and continuously recycled to the reactor. The return of free, unreacted fatty acids to the reaction vessel insures excess free fatty acids in the reaction and permits conversion at a faster pace.

The reaction is essentially complete in approximately 4 hours at 240° C., and both fatty acids and water stop accumulating in the separator. At this point, the return of the fatty acids is discontinued and a progressive reduction in pressure is applied from 5" of vacuum through approximately 29" of vacuum and the temperature maintained at 238° C.–240° C. over the next approximately 2–4 hours while collecting the distillates for the purpose of stripping the free fatty acids, i.e., removing the unreacted fatty acids of the initial charge.

Any incidental interface that has some fatty acids may or may not be returned to the reaction mass, and preferably are not returned to avoid return of moisture to the reactor. By "incidental interface" is meant mixtures of water and fatty acids in the separator in the form of emulsions or dispersions.

The progress of the reaction is followed analytically by titrating free fatty acids (FFA) against a normal solution of sodium hydroxide as is well known by those skilled in the art to track the decline in fatty acid content and the increase in the amount of ester formed as the reaction progresses toward completion. Preferably, titration is by way of the Epton method commonly used for anionic surfactants. The reaction is considered sufficiently complete when FFA are approximately 15 wt. % to 18 wt. % in the residual mass in the reactor. Stated otherwise, the reaction proceeds until only about 15 wt. % to 18 wt. % of the reactor contents comprises free fatty acids, the remainder comprising SCI product and a small percentage of unreacted NIS, if any. Typically, the time required for near completion of the reaction is approximately 4 hours at reaction temperatures, at which time the return of the fatty acids is discontinued.

The free fatty acids (FFA) are then removed from the reaction mass by stripping, preferably at sub-atmospheric conditions at a temperature in the range of 200° C. to 250° C., more preferably at about 220° C. to 250° C., and most preferably at about 240° C., as is well-known in the art. A vacuum is slowly applied to the reaction vessel to distill off excess fatty acids. The fatty acids which are distilled off are recovered and recycled back into subsequent productions. The SCI product mass in the reactor is fluid. The vacuum is then released under nitrogen flow and the mass is discharged hot for the purpose of flaking on the belt flaker. The flaking process is well-known in the art.

The ester products prepared by the process of the invention are stable, i.e., are not subject to appreciable change in pH upon storage, and are useful in formulating cosmetics, skin care products, personal care products such as body washes, cleansers, creams, lotions, shampoos, and other topical applications and products.

The process of the invention results in none or negligible deviation in the molecular weight distribution of the SCI product as compared to commercially available SCI products, as well as there being no discrepancy in accounting for all 100 parts of the starting coco fatty acids (CFA). The process permits for accountability approaching 99% of the parts of the composition.

The carbon chain distribution of the reactants and product is determined by gas chromatography. Prior art SCI products have different carbon chain distributions than the initial reactants and have altered carbon chain distribution of the residual free fatty acids by design. By "residual free fatty acids" is meant the 15%–18% FFA remaining in the reactor at the completion of the reaction.

The esters of the invention show only 1–2% loss of SCI Activity and a corresponding increase in percentage of free fatty acids. SCI Activity is defined as anionic active matter as SCI, or, in other words, the activity of SCI measured as the amount of SCI which is actually present in the reaction mixture as determined by titrimetric analysis, as described above. Stated simply, SCI Activity is the amount of SCI product formed. The SCI products of the prior art degrade upon long holding periods at high temperature to the extent of about 2–5% loss of Activity and a proportionate increase in percentage of free fatty acids. When this happens to the prior art SCI products, a GAP is generated due to the increased amount of free NIS and residual free fatty acids by way of the possible reversal of reaction. The SCI product of the invention undergoes none to negligible degradation over long holding periods.

The prior art products analyze to give SCI Activity and unreacted, residual FFA total at about 92% by the assigned molecular weights and 94% by the adjusted molecular weights. The assigned molecular weights of both acid and zinc catalyzed SCI for SCI Activity and residual FFA respectively are 338 and 208 while the adjusted weights from the analysis respectively are 345 and 217. In either case of the calculations, there is still a GAP that is wide enough to account for 100% of the compositions of the prior art SCI products. This reflects the pronounced change in the carbon chain distribution of the prior art SCI products and the presence of soap like species.

In contrast, the SCI products of the invention analyze to give an SCI Activity and residual FFA total of about 97% using assigned molecular weights (i.e., genuine mol. wts.) derived from the starting raw fatty acids rather than the altered/adjusted mol. wts. The difference [(100−(Activity+ FFA)] equates to the unreacted NIS+some inorganic matter and others. Thus, the conversion of NIS is almost complete, resulting in formation of an SCI product of a genuine molecular weight rather than an altered/adjusted molecular weight.

Any distillate fatty acids (DFA) that come off are re-usable instantly in the immediate subsequent production rather than accumulating them as by-products. This is not a selective return of fatty acids: all distillate fatty acids are returned thereby reducing or eliminating accumulation of by-product Distillate Fatty Acids (DFA). Return and reuse of distillate fatty acids (DFA) do not cause deviation to the C-chain distribution of the range of specifications of the starting coco fatty acids (CFA) when added at 15 parts of DFA to 85 parts of CFA.

Gas chromatography analysis of the C-chain distribution shows that the anionic active SCI molecular weight distribution has not changed. The residual FFA remains about the same having a molecular weight close to or equal to the molecular weight of the starting coco fatty acids. The stripped DFA does show proportionately higher amounts of C8–C10 and C12 fatty acids but this does not affect the molecular weight distribution of the already formed anionic SCI product of the invention. The escape of the C8, C10 acids occurs after the fact, i.e., after the formation of the SCI which may be beneficial in avoiding the presence of these lower fatty acids due to their known irritation characteristics in the personal care cleansing products/formulations or toilet bar soaps.

Thus, the esterification reaction of the invention is conducted in the absence of a catalyst, in a closed system, with return of all distillate fatty acids for maximum utilization to obtain high yields of a soap-free SCI product with high color, odor and activity integrity, where there is minimal or negligible change in the molecular weight distribution of the SCI product as compared to prior art acid or zinc catalyzed SCI products.

The process does not require selective removal of lower molecular weight fatty acids up-front. Neither does the process require selective addition of higher fatty acids to achieve fluidity of the reaction mass, which is usually done at the expense of reducing the foaming characteristics of the SCI product. The resulting product integrity is equal to or better than those SCI products prepared by prior art processes which employ a catalyst during the reaction.

Table I is a Table of Identification which identifies SCI products, both known and produced by the process of this invention. For ease of identification, each ester is identified by an Example Number, and a Trade Name, where available. This identification system is used in the subsequent Tables II through XI.

By "acid catalyzed" is meant catalysts comprising acids and acid formers, including salts of strong acids and weak bases. By "zinc catalyzed" is meant catalysts comprising zinc oxide and mixtures of zinc oxide, soluble zinc salts, and soaps formed with zinc oxide.

TABLE I

SCI-PRODUCT IDENTIFICATION FOR TABLES I–XI

| Compound/ Example No. | Process New Invention Uncatalysed | Process Known Acid Catalyzed | Process Known Zinc Catalyzed |
|---|---|---|---|
| A | − | + | − |
| B | − | − | + |
| C | + | − | − |
| D | + | − | − |
| E | + | − | − |
| F | − | + | − |
| G | − | − | + |
| H | − | + | − |
| I | − | − | + |
| J | − | − | + |
| K | − | − | + |
| L | + | − | − |
| M | + | − | − |
| N | + | − | − |
| O | + | − | − |
| P | + | − | − |
| Q | − | − | + |
| R | − | − | + |
| S | − | − | + |
| T | + | − | − |
| U | + | − | − |
| V | + | − | − |
| W | + | − | − |
| X | − | + | − |
| Y | − | − | + |
| Z | + | − | − |
| VV | − | − | + |

TABLE I-continued

SCI-PRODUCT IDENTIFICATION FOR TABLES I–XI

| Compound/ Example No. | Process New Invention Uncatalysed | Process Known Acid Catalyzed | Process Known Zinc Catalyzed |
|---|---|---|---|
| WW | + | − | − |
| XX | − | + | − |
| YY | − | − | + |
| PURIFIED: | | | |
| CP | + | − | − |
| DP | + | − | − |
| HP | − | + | − |
| IP | − | − | + |
| JP | − | − | + |

Preparation of the esters of the invention is illustrated by the following non-limiting examples. In the examples, as well as throughout this application, the chemical and scientific symbols have their customary meanings and all percents are weight percents unless otherwise specified.

In the following discussion, TAURANOL® I-78 and TAURANOL® I-78E are registered trademarks of Finetex, Inc., Elmwood Park, N.J., 07407. TAURANOL® I-78 is an SCI product of an acid catalyzed reaction while TAURANOL® I-78E is an SCI product of a zinc catalyzed reaction. Jordapong CI is a registered trademark of PPG Industries, Gurnee, Ill. HOSTAPON® SCI-85 is a registered trademark of Hoechst–Celanese Corp., Pasadena, Tex. Both Jordapon® CI and Hostapon® SCI-85 are SCI products of zinc catalyzed reactions.

EXAMPLES A & B

The compounds in Examples A & B are TAURANOL® I-78 and TAURANOL® I-78E, respectively, commercially available from Finetex, Inc., Elmwood Park, N.J., 07407. TAURANOL® I-78 is an SCI product of an acid catalyzed reaction while TAURANOL® I-78E is an SCI product of a zinc catalyzed reaction.

EXAMPLE C (SCI Product of the Invention)

To a stainless steel vessel (of approximately 50 gal. capacity), equipped with high temperature heating (by hot oil) jacket, condenser and receiver, and mixing, under nitrogen, was charged 217 lbs. of sodium isethionate and pre-melted 233 lbs. coco fatty acids. The sodium isethionate (Hostapon® SI, Hoechst Celanese) was assayed at 57.6% activity as hydroxyethane sulfonic acid sodium salt, had alkalinity of 0.27 mgms. KOH/gm and acidity of 0 mg KOH/g. The coco fatty acids used was EMERY® 626 (Henkel Corp., Cincinnati, Ohio) and was pre-melted at 110° F.–120° F. (44° C.–49° C.) before charging to the vessel.

The mixture was brought to 465° F. (240° C.) over 4–4.5 hrs., during which period water of dilution and some of the water of reaction was collected with the return of any fatty acids that azeotroped from the reaction vessel. The water collected was 85 lbs. The reaction mixture was held at 465° F. (240° C.) for three hours while returning the fatty acids back to the vessel. Thereafter, the reaction mass was held at 465° F. (240° C.) for the next hour and the fatty acids that distilled off were collected along with any remaining water of reaction. The product mass in the reactor was then progressively subjected to reduced pressure of 10" vacuum to approximately 27" vacuum over the next 1–1.5 hours. Fatty acids distilled off and collected were 31 lbs.

The product mass in the reactor was fluid and of very, very light color without any indications of discoloration. The vacuum was then released under nitrogen flow and the mass was then discharged hot for the purpose of flaking on a belt flaker. A yield of 291 lbs. was collected as flaked and solid material. The final product had the following analysis:

Appearance: White flakes
% Activity (338): 83.76
% Free Fatty Acid (208): 12.17
Acidity mg KOH/g: 32.84
pH (10%): 5.25
Color: APHA<10
Odor: Excellent, non-offensive
Alkalinity mg KOH/g: 0
Gap: 4.07

EXAMPLE D
(SCI Product of The Invention)

A large reactor vessel of approximately 2000 gal. capacity was used for this experiment. The vessel was equipped with condenser, receiver and high temperature heating and cooling capabilities, nitrogen flow and continuous recording of temperatures were provided on the vessel. Variable mixing was also provided for proper and efficient mixing.

Under nitrogen atmosphere, 7100 lbs. of sodium isethionate of the same analysis as in Example C. was charged to the reaction vessel. 7600 lbs. of pre-melted (110° F.) coco fatty acids (EMERY® 626) were charged.

The reaction vessel, i.e. reactor temperature, was then brought to 450° F. (232° C.) over 3.5–4 hrs. Any water that distilled off was collected along with any incidental interface of fatty acids. The temperature was then raised to 465° F. (240° C.) over the next 1–1.25 hrs. The water collected so far was 3160 lbs. and fatty acid was 42 lbs. The reactor mass was held at 460° F.–465° F. (238° C.–240° C.) while returning the distilled fatty acids to the reaction vessel continuously without any refurbishments, (i.e., without adding additional, external material) and collecting the water that distilled off. This was accomplished over a period of 2–3 hours. After this stage, the return of the fatty acids was discontinued and a progressive reduction in pressure was applied from 5" of vacuum through 25" vacuum over a 2 hr. period. Thereafter, pressure was reduced further to approximately 28"–29" of vacuum and the temperature maintained at 460° F.–465° F. (238° C.–240° C.) over the next 1–1.5 hrs. while collecting the distillates for the purpose of stripping the free fatty acids. The free fatty acids distilled off and collected were of very light color and weighed 1360 lbs. The batch mass in the vessel was then brought to over 760 mm. Hg under nitrogen and then discharged for flaking on the belt flaker by the known practice in the trade. The flaking time involved was approximately 8–9 hours. A yield of 9723 lbs. was obtained which was very, very light in color and had none to negligible odor.

The product of this experiment had the following analysis:

% Activity (338): 84.87
% Free Fatty Acid (208): 10.84
Acidity mg KOH/g: 29.26
pH (10%): 5.0
Color (APHA):<10
Appearance: White flakes
Gap: 4.29

EXAMPLE E
(SCI Product of The Invention)
Preparation of Sodium Cocoyl Isethionate In 1000 ml. four neck round bottom flask equipped with glass stirrer, Dean Stark receiver, condenser and thermometer was added 333.69 grams of sodium isethionate (Hostapon® SI, Hoechst Celanese, % activity—57.6; alkalinity—0.25 mg KOH/g; pH—8.95) and 362.62 grams of pre-melted coco fatty acid (EMERY® 626). The temperature was raised to 170° C. with good flow of nitrogen to remove the water of dilution and water of reaction from sodium isethionate. The reaction mixture was then raised to 240° C. in the next 60 minutes and held there for three hours. During this hold period, fatty acids that escaped the reaction mass were returned to the reaction mass. Any incidental interface that had some fatty acids was not returned to the reaction mass. Progress of the reaction was followed by titrating free fatty acid and anionic actvity by methylene blue titration. The following intercept samples were analyzed during the three hour hold period:

| Hold Period | Acid Value/Free Fatty Acids (208) | | Activity (338) |
| --- | --- | --- | --- |
|  | mgms KOH/gm./ | % | % |
| 0 hr. | 160/ | 59.32 | 0 |
| 1 hr. | 140/ | 51.90 | 16.3 |
| 2 hrs. | 82/ | 30.40 | 60.1 |
| 3 hrs. | 70.12/ | 26.00 | 68.3 |

The acid value is obtained by titration against normal sodium hydroxide and is expressed in mgms KOH/gm.

The distillate (water of dilution & water of reaction) collected was 162.5 grams against theoretical estimate of 163.52 grams. The free fatty acids (approximately 54.40 grams) were then removed from the reaction mass by stripping at 240° C. in the next 60 minutes. The product, sodium cocoyl isethionate, (SCI), was then discharged and flaked and had the following analysis:

Yield: 475 grams
% Free Fatty Acid (208): 12.14
% Activity (338): 84.88
pH (10%): 4.3
Gap: 2.98

EXAMPLE F
(Acid Catalyzed SCI Product)
Preparation of Sodium Cocoyl Isethionate

In 1000 ml. four neck round bottom flask equipped with glass stirrer, Dean Stark receiver, condenser and thermometer was added 333.69 grams of sodium isethionate (Hostapon® SI, Hoechst Celanese, % activity—57.6; alkalinity—0.90 mg KOH/g; pH—12.95) and 362.62 grams of pre-melted coco fatty acid (EMERY® 626) and 0.21 grams of methane sulfonic acid. The temperature was raised to 170° C. with good flow of nitrogen to remove the water of dilution from sodium isethionate. The reaction mixture was then raised to 240° C. in the next 60 minutes and held there for three hours. During this hold period, fatty acids that escaped the reaction mass were returned to the reaction mass. Any incidental interface that had some fatty acids was not returned to the reaction mass. Progress of the reaction was followed by titrating free fatty acid and anionic activity by methlyene blue titration. The following intercept samples were analyzed during the three hour hold period:

| Hold Period | Acid Value/Free Fatty Acids (208) mgms KOH/gm./ | % | Activity (338) % |
|---|---|---|---|
| 0 hr. | 160/ | 59.32 | 0 |
| 1 hr. | 148/ | 54.87 | 12.2 |
| 2 hrs. | 98/ | 36.33 | 47.88 |
| 3 hrs. | 78/ | 28.92 | 62.10 |

The distillate (water of dilution & water of reaction) collected was 157 grams against theoretical estimate of 163.52 grams. The free fatty acids (approximately 54.40 grams) were then removed from reaction mass by stripping at 240° C. in the next 60 minutes. The product, sodium cocoyl isethionate, was then discharged and flaked and had the following analysis:

Yield: 480 grams
% Free Fatty Acid (208): 11.12
% Activity (338): 80.32
pH (10%): 4.30
Gap: 8.56

EXAMPLE G
(Zinc Catalyzed SCI Product)
Preparation of Sodium Cocoyl Isethionate In 1000 ml. four neck round bottom flask equipped with glass stirrer, Dean Stark receiver, condenser and thermometer was added 333.69 grams of sodium isethionate (Hostapon® SI, Hoechst Celanese, % activity—57.6; alkalinity—0.90 mg KOH/g; pH—12.95) and 362.62 grams of pre-melted coco fatty acid (EMERY® 626) and 0.77 grams of zinc oxide. The temperature was raised to 170° C. with good flow of nitrogen to remove the water of dilution from sodium isethionate. The reaction mixture was then raised to 240° C. in the next 60 minutes and held there for three hours. During this hold period, fatty acids that escaped the reaction mass were returned to the reaction mass. Any incidental interface that had some fatty acids was not returned to the reaction mass. Progress of the reaction was followed by titrating free fatty acid and anionic activity by methylene blue titration. The following intercept samples were analyzed during the three hour hold period:

| Hold Period | Acid Value/Free Fatty Acids (208) mgms KOH/gm./ | % | Activity (338) % |
|---|---|---|---|
| 0 hr. | 156/ | 57.8 | 8.98 |
| 1 hr. | 150/ | 55.61 | 10.10 |
| 2 hrs. | 109/ | 40.41 | 42.10 |
| 3 hrs. | 88/ | 32.62 | 58.80 |

The distillate (water of dilution & water of reaction) collected was 156 grams against theoretical estimate of 163.52 grams. The free fatty acids (approximately 54.40 grams) were then removed from reaction mass by stripping at 240° C. in the next 60 minutes. The product, sodium cocoyl isethionate, was then discharged and flaked and had the following analysis:

Yield: 476 grams
% Free Fatty Acid (208): 12.05
% Activity (338): 78.95
pH (10%): 5.1
Gap: 9.0

EXAMPLES H, I, J, & K

The compounds of Examples H, I, J & K are TAURANOL® I-78, TAURANOL® I-78E, Jordapon CI, and HOSTAPON® SCI-85 respectively, which are commercially available.

EXAMPLE L
(SCI Product of Invention)
Preparation of Sodium Cocoyl Isethionate In 1000 ml. four neck round bottom flask equipped with glass stirrer, Dean Stark receiver, condenser and thermometer was added 333.69 grams of sodium isethionate (Hostapon® SI, Hoechst Celanese, % activity—57.6; alkalinity—0.30 mg KOH/g; pH—8.98) and 362.62 grams of pre-melted coco fatty acid (EMERY® 626). The temperature was raised to 170° C. with good flow of nitrogen to remove the water of dilution from sodium isethionate. The reaction mixture was then raised to 240° C. in the next 60 minutes and held there for two hours. During this hold period, fatty acids that escaped the reaction mass were returned to the reaction mass. Any incidental interface that had some fatty acids was not returned to the reaction mass. The distillate (water of dilution & water of reaction) collected was 161.00 grams against theoretical estimate of 163.52 grams. The free fatty acids (approximately 54.40 grams) were then removed from reaction mass by stripping at 240° C. in the next 60 minutes. The product, sodium cocoyl isethionate, was then discharged and flaked and had the following analysis:

Yield: 480 grams
% Free Fatty Acid (208): 12.06
% Activity (338): 83.24
pH (10%): 5.2
Gap: 4.7

EXAMPLE M
(SCI Product of Invention)
Preparation of Sodium Cocoyl Isethionate In 1000 ml. four neck round bottom flask equipped with glass stirrer, Dean Stark receiver, condenser and thermometer was added 333.69 grams of sodium isethionate (Hostapon® SI, Hoechst Celanese, % activity—57.6; alkalinity—0.30 mg KOH/g; pH—8.98) and 362.62 grams of pre-melted coco fatty acid (EMERY® 626). The temperature was raised to 170° C. with good flow of nitrogen to remove the water of dilution from sodium isethionate. The reaction mixture was then raised to 240° C. in the next 60 minutes and held for three hours. During this hold period, fatty acids that escaped the reaction mass were returned to the reaction mass. Any incidental interface that had some fatty acids was not returned to the reaction mass. The distillate (water of dilution & water of reaction) collected was 161 grams against theoretical estimate of 163.52 grams. The free fatty acids (approximately 54.40 grams) were then removed from reaction mass by stripping at 240° C. in the next 60 minutes. The product, sodium cocoyl isethionate, was then discharged and flaked and had the following analysis:

Yield: 480 grams
% Free Fatty Acid (208): 9.90
% Activity (338): 88.48
pH (10%): 4.2

Gap: 1.62
Conclusion: The GAP is very small

EXAMPLE N
(SCI Product of Invention)
Preparation of Sodium Cocoyl Isethionate In 1000 ml. four neck round bottom flask equipped with glass stirrer, Dean Stark receiver, condenser and thermometer was added 333.69 grams of sodium isethionate (Hostapon® SI, Hoechst Celanese, % activity—57.6; alkalinity—0.30 mg KOH/g; pH—8.98) and 362.62 grams of pre-melted coco fatty acid (EMERY® 626). The temperature was raised to 170° C. with good flow of nitrogen to remove the water of dilution from sodium isethionate. The reaction mixture was then raised to 240° C. in the next 60 minutes and held for three hours. During this hold period, fatty acids that escaped the reaction mass were returned to the reaction mass. Any incidental interface that had some fatty acids was not returned to the reaction mass. The distillate (water of dilution & water of reaction) collected was 161 grams against theoretical estimate of 163.52 grams. The free fatty acids (approximately 54.40 grams) were then removed from reaction mass by stripping at 240° C. in the next 60 minutes. The product, sodium cocoyl isethionate, was then discharged and flaked and had the following analysis:

Yield: 482 grams
% Free Fatty Acid (208): 13.86
% Activity (338): 82.55
pH (10%): 4.3
Gap: 3.56

EXAMPLE O
(SCI Product of The Invention—pH/Alkalinity Comparison)
Preparation of Sodium Cocoyl Isethionate In 1000 ml. four neck round bottom flask equipped with glass stirrer, Dean Stark receiver, condenser and thermometer was added 333.69 grams of sodium isethionate (Hostapon® SI, Hoechst Celanese, % activity—57.6; alkalinity—1.08 mg KOH/g; pH—12.0) and 362.62 grams of pre-melted coco fatty acid (EMERY® 626). The temperature was raised to 170° C. with good flow of nitrogen to remove the water of dilution from sodium isethionate. The reaction mixture was then raised to 240° C. in the next 60 minutes and held for three hours. During this hold period, fatty acids that escaped the reaction mass were returned to the reaction mass. Any incidental interface that had some fatty acids was not returned to the reaction mass. The distillate (water of dilution & water of reaction) collected was 158.4 grams against theoretical estimate of 163.52 grams. The free fatty acids (approximately 54.40 grams) were then removed from reaction mass by stripping at 240° C. in the next 60 minutes. The product, sodium cocoyl isethionate, was then discharged and flaked and had the following analysis:

Yield: 484 grams
% Free Fatty Acid (208): 12.27
% Activity (338): 81.25
pH (10%): 5.50
Gap: 6.48

Conclusion: GAP is relatively higher than in the invention examples, where alkalinity of NIS is close to or greater than 0.75 mgms. KOH/gm., contrary to Example M.

EXAMPLE P
(SCI Product of the Invention—pH/Alkalinity Comparison)
Preparation of Sodium Cocoyl Isethionate In 1000 mi. four neck round bottom flask equipped with glass stirrer, Dean Stark receiver, condenser and thermometer was added 333.69 grams of sodium isethionate (Hostapon® SI, Hoechst Celanese, % activity—57.6; alkalinity—1.08 mg KOH/g; pH—12.0) and 362.62 grams of pre-melted coco fatty acid (EMERY® 626). The temperature was raised to 170° C. with good flow of nitrogen to remove the water of dilution from sodium isethionate. The reaction mixture was then raised to 240° C. in the next 60 minutes and held for three hours. During this hold period, fatty acids that escaped the reaction mass were returned to the reaction mass. Any incidental interface that had some fatty acids was not returned to the reaction mass. The distillate (water of dilution & water of reaction) collected was 157.70 grams against theoretical estimate of 163.52 grams. The free fatty acids (approximately 54.40 grams) were then removed from reaction mass by stripping at 240° C. in the next 60 minutes. The product, sodium cocoyl isethionate, was then discharged and flaked and had the following analysis:

Yield: 480 grams
% Free Fatty Acid (208): 13.93
% Activity (338): 78.61
pH (10%): 5.62
Gap: 7.45

In conclusion, when the alkalinity of NIS is over 0.75 mgms. KOH/gm., the GAP increases.

EXAMPLE Q
(Zinc Catalyzed SCI Product—Low Alkalinity/pH Comparison)
Preparation of Sodium Cocoyl Isethionate In 1000 ml. four neck round bottom flask equipped with glass stirrer, Dean Stark receiver, condenser and thermometer was added 333.69 grams of sodium isethionate (Hostapon® SI, Hoechst Celanese, % activity—57.6; alkalinity—0.30 mg KOH/g; pH—8.95) and 362.62 grams of pre-melted coco fatty acid (EMERY® 626) and 0.77 grams of zinc oxide. The temperature was raised to 170° C. with good flow of nitrogen to remove the water of dilution from sodium isethionate. The reaction mixture was then raised to 227° C. in the next 60 minutes and held for two hours. During this hold period, fatty acids that escaped the reaction mass were returned to the reaction mass. Any incidental interface that had some fatty acids was not returned to the reaction mass. The distillate (water of dilution & water of reaction) collected was 156 grams against theoretical estimate of 163.52 grams. The free fatty acids (approximately 54.40 grams) were then removed from reaction mass by stripping at 227° C. in the next 60 minutes. The product, sodium cocoyl isethionate, was then discharged and flaked and had the following analysis:

Yield: 482 grams
% Free Fatty Acid (208): 17.33
% Activity (338): 76.85
pH (10%): 5.60
Gap: 5.81

In conclusion, even in the case of the presence of a catalyst and low alkalinity of NIS, the GAP is higher than the product of the invention.

EXAMPLE R
(Zinc Catalyzed SCI Product—Low pH/Alkalinity Comparison)
Preparation of Sodium Cocoyl lsethionate In 1000 ml. four neck round bottom flask equipped with glass stirrer, Dean Stark receiver, condenser and thermometer was added 333.69 grams of sodium isethionate (Hostapong SI, Hoechst Celanese, % activity—57.6; alkalinity—0.30 mg KOH/g; pH—8.95) and 362.62 grams of pre-melted coco fatty acid (EMERY® 626) and 0.77 grams of zinc oxide. The temperature was raised to 170° C. with good flow of nitrogen to remove the water of dilution from sodium isethionate. The reaction mixture was then raised to 227° C. in the next 60 minutes and held for two hours. During this hold period, fatty acids that escaped the reaction mass were returned to the reaction mass. Any incidental interface that had some fatty acids was not returned to the reaction mass. The distillate (water of dilution & water of reaction) collected was 155 grams against theoretical estimate of 163.52 grams. The free fatty acids (approximately 54.40 grams) were then removed from reaction mass by stripping at 227° C. in the next 60 minutes. The product, sodium cocoyl isethionate, was then discharged and flaked and had the following analysis:

Yield: 485 grams

% Free Fatty Acid (208): 10.4

% Activity (338): 84.08 pH (10%): 5.8

Gap: 5.52

In conclusion, even where the alkalinity and pH are low, the zinc catalyzed reaction still shows a higher GAP than the product of the invention.

EXAMPLE S
(Zinc Catalyzed SCI Product—High Alkalinity/pH Comparison)
Preparation of Sodium cocoyl Isethionate In 1000 ml. four neck round bottom flask equipped with glass stirrer, Dean Stark receiver, condenser and thermometer was added 333.69 grams of sodium isethionate (Hostapon® SI, Hoechst Celanese, % activity—57.6; alkalinity—1.51 mg KOH/g; pH—9.10) and 362.62 grams of pre-melted coco fatty acid (EMERY® 626) and 0.77 grams of zinc oxide. The temperature was raised to 170° C. with good flow of nitrogen to remove the water of dilution from sodium isethionate. The reaction mixture was then raised to 227° C. in the next 60 minutes and held for two hours. During this hold period, fatty acids that escaped the reaction mass were returned to the reaction mass. Any incidental interface that had some fatty acids was not returned to the reaction mass. The distillate (water of dilution & water of reaction) collected was 155 grams against theoretical estimate of 163.52 grams. The free fatty acids (approximately 54.40 grams) were then removed from reaction mass by stripping at 227° C. in the next 60 minutes. The product, sodium cocoyl isethionate, was then discharged and flaked and had the following analysis:

Yield: 485 grams

% Free Fatty Acid (208): 14.40

% Activity (338): 77.56 pH (10%): 5.6

Gap: 8.04

In conclusion, higher alkalinity of NIS even in zinc catalyzed product gives higher GAP than product of the invention.

EXAMPLE T
(SCI Product of Invention—High Alkalinity Comparison)
Preparation of Sodium Cocoyl Isethionate In 1000 ml. four neck round bottom flask equipped with glass stirrer, Dean Stark receiver, condenser and thermometer was added 333.69 grams of sodium isethionate (Witco, USA % activity—56.1, alkalinity—1.51 mg KOH/g; pH—9.1) and 362.62 grams of pre-melted coco fatty acid (EMERY® 626). The temperature was raised to 170° C. with good flow of nitrogen to remove the water of dilution from sodium isethionate. The reaction mixture was then raised to 240° C. in the next 60 minutes and held for three hours. During this hold period, fatty acids that escaped the reaction mass were returned to the reaction mass. Any incidental interface that had some fatty acids was not returned to the reaction mass. The distillate (water of dilution & water of reaction) collected was 162 grams against theoretical estimate of 164.86 grams. The free fatty acids (approximately 54.9 grams) were then removed from reaction mass by stripping at 240° C. in the next 60 minutes. The product, sodium cocoyl isethionate, was then discharged and flaked and had the following analysis:

Yield: 475 grams

% Free Fatty Acid (208): 13

% Activity (338): 81.60 pH (10%): 5.7

Gap: 5.4

In conclusion, uncatalyzed invention product, even at higher alkalinity of NIS, gives lower GAP than zinc catalyzed product.

EXAMPLE U
(SCI Product of the Invention)
Preparation of Sodium Cocoyl Isethionate In 1000 ml. four neck round bottom flask equipped with glass stirrer, Dean Stark receiver, condenser and thermometer was added 333.69 grams of sodium isethionate (Hostapon® SI, Hoechst Celanese, % activity—57.6; alkalinity—0.25 mg KOH/g; pH—8.75) and 362.62 grams of pre-melted coco fatty acid (EMERY® 626). The temperature was raised to 170° C. with good flow of nitrogen to remove the water of dilution from sodium isethionate. The reaction mixture was then raised to 240° C. in the next 60 minutes and held for three hours. During this hold period, fatty acids that escaped the reaction mass were returned to the reaction mass. Any incidental interface that had some fatty acids was not returned to the reaction mass. The distillate (water of dilution & water of reaction) collected was 163 grams against theoretical estimate of 163.52 grams. The free fatty acids (approximately 54.40 grams) were then removed from reaction mass by stripping at 240° C. in the next 60 minutes. The product, sodium cocoyl isethionate, was then discharged and flaked and had the following analysis:

Yield: 476 grams

% Free Fatty Acid (208): 12.01

% Activity (338): 85.55 pH (10%): 5.0

Gap: 2.44

In conclusion, very low GAP in the process of the Invention.

EXAMPLE V
(SCI Product of Invention)
Preparation of Sodium Cocoyl Isethionate In 1000 ml. four neck round bottom flask equipped with glass stirrer, Dean Stark receiver, condenser and thermometer was added 355.04 grams of sodium isethionate (Hostapon® SI, Hoechst Celanese, % activity—57.6; alkalinity—0.25 mg KOH/g; pH—9.50) and 344.96 grams of pre-melted coco fatty acid (EMERY® 626). The temperature was raised to 170° C. with good flow of nitrogen to remove the water of dilution from sodium isethionate. The reaction mixture was then raised to 240° C. in the next 60 minutes and held for three hours. During this hold period, fatty acids that escaped the reaction mass were returned to the reaction mass. Any incidental interface that had some fatty acids was not returned to the reaction mass. The distillate (water of dilution & water of reaction) collected was 168.50 grams against theoretical estimate of 173.98 grams. The free fatty acids (approximately 34.5 grams) were then removed from reaction mass by stripping at 240° C. in the next 60 minutes. The product, sodium cocoyl isethionate, was then discharged and flaked and had the following analysis:

Yield: 492 grams
% Free Fatty Acid (208): 13.56
% Activity (338): 82.08
pH (10%): 5.1
Gap: 4.36

In conclusion, the GAP is not very high, below 5.0, where the alkalinity is low and the pH is high.

EXAMPLE W
(SCI Product of Invention—Comparison Low Alkalinity)
Preparation of Sodium Cocoyl Isethionate In 1000 ml. four neck round bottom flask equipped with glass stirrer, Dean Stark receiver, condenser and thermometer was added 355.04 grams of sodium isethionate (Hostapon® SI, Hoechst Celanese, % activity—57.6; alkalinity—0.25 mg KOH/g; pH—9.50) and 344.96 grams of pre-melted coco fatty acid (EMERY® 626). The temperature was raised to 170° C. with good flow of nitrogen to remove the water of dilution from sodium isethionate. The reaction mixture was then raised to 240° in the next 60 minutes and held for four hours. During this hold period, fatty acids that escaped the reaction mass were returned to the reaction mass. Any incidental interface that had some fatty acids was not returned to the reaction mass. The distillate (water of dilution & water of reaction) collected was 168 grams against theoretical estimate of 173.98 grams. The free fatty acids (approximately 34.5 grams) were then removed from reaction mass by stripping at 240° C. in the next 60 minutes. The product, sodium cocoyl isethionate, was then discharged and flaked and had the following analysis:

Yield: 490 grams
% Free Fatty Acid (208): 10.38
% Activity (338): 85.51
pH (10%): 4.8
Gap: 4.10

In conclusion, there is a low GAP, well below 5.0, where the alkalinity is low and the pH is higher.

EXAMPLE X
(Acid Catalyzed SCI Product)
Preparation of Sodium Cocoyl Isethionate In 1000 ml. four neck round bottom flask equipped with glass stirrer, Dean Stark receiver, condenser and thermometer was added 333.69 grams of sodium isethionate (Witco, USA, % activity—57.6; alkalinity—0.70 mg KOH/g; pH—11.90) and 362.62 grams of pre-melted coco fatty acid (EMERY® 626) and 0.20 grams of methane sulfonic acid. The temperature was raised to 170° C. with good flow of nitrogen to remove the water of dilution from sodium isethionate. The reaction mixture was then raised to 240° C. in the next 60 minutes and held there for two hours. During this hold period, fatty acids that escaped the reaction mass were returned to the reaction mass. Any incidental interface that had some fatty acids was not returned to the reaction mass. The distillate (water of dilution & water of reaction) collected was 155 grams against theoretical estimate of 163.52 grams. The free fatty acids (approximately 54.40 grams) were then removed from reaction mass by stripping at 240° C. in the next 60 minutes. The product, sodium cocoyl isethionate, was then discharged and flaked and had the following analysis:

Yield: 485 grams
% Free Fatty Acid (208): 14.96
% Activity (338): 76.38
pH (10%): 4.0
Gap: 8.66

In conclusion, acid catalyzed SCI product, with high alkalinity and high pH, has a very high GAP, even when following the process of the invention, other than the catalyst.

EXAMPLE Y
(Zinc Catalyzed SCI Product—High pH Comparison)
Preparation of Sodium Cocoyl Isethionate In 1000 ml. four neck round bottom flask equipped with glass stirrer, Dean Stark receiver, condenser and thermometer was added 333.69 grams of sodium isethionate (Witco, % activity—57.6; alkalinity—0.70 mg KOH/g; pH—11.90) and 362.62 grams of pre-melted coco fatty acid (EMERY® 626) and 0.77 grams of zinc oxide. The temperature was raised to 170° C. with good flow of nitrogen to remove the water of dilution from sodium isethionate. The reaction mixture was then raised to 240° C. in the next 60 minutes and held for two hours. During this hold period, fatty acids that escaped the reaction mass were returned to the reaction mass. Any incidental interface that had some fatty acids was not returned to the reaction mass. The distillate (water of dilution & water of reaction) collected was 154 grams against theoretical estimate of 163.52 grams. The free fatty acids (approximately 54.40 grams) were then removed from reaction mass by stripping at 240° C. in the next 60 minutes. The product, sodium cocoyl isethionate, was then discharged and flaked and had the following analysis:

Yield: 481 grains
% Free Fatty Acid (208): 11.21
% Activity (338): 81.72
pH (10%): 5.8
Gap: 7.07

In conclusion, zinc catalyzed SCI product, with higher alkalinity and higher pH, gives a high GAP product even when we apply process of the invention, other than the catalyst.

EXAMPLE Z
(SCI Product of Invention—High pH Comparison)
Preparation of Sodium Cocoyl Isethionate In 1000 ml. four neck round bottom flask equipped with glass stirrer, Dean Stark receiver, condenser and thermometer was added 333.69 grams of sodium isethionate (Witco, % activity—57.6; alkalinity—0.168 mg KOH/g; pH—8.53) and 362.62 grams of pre-melted coco fatty acid (EMERY® 626). The temperature was raised to 170° C. with good flow of nitrogen to remove the water of dilution from sodium isethionate. The reaction mixture was then raised to 240° C. in the next 60 minutes and held for two hours. During this hold period, fatty acids that escaped the reaction mass were returned to the reaction mass. Any incidental interface that had some fatty acids was not returned to the reaction mass. The distillate (water of dilution & water of reaction) collected was 162 grams against theoretical estimate of 163.52 grams. The free fatty acids (approximately 54.40 grams) were then removed from reaction mass by stripping at 240° C. in the next 60 minutes. The product, sodium cocoyl isethionate, was then discharged and flaked and had the following analysis.

Yield: 476 grams
% Free Fatty Acid (208): 11.00
% Activity (338): 84.79
pH (10%): 3.75
Gap: 4.21

In conclusion, even with moderate pH and low alkalinity, the process of the invention gives a low GAP product.

EXAMPLE VV
(Zinc Catalyzed SCI Product—High pH/Alkalinity Comparison)
Preparation of Sodium Cocoyl Isethionate In 1000 ml. four neck round bottom flask equipped with glass stirrer, Dean Stark receiver, condenser and thermometer was added 333.69 grams of sodium isethionate (Witco, % activity—57.6; alkalinity—0.76 mg KOH/g; pH—11.90) and 362.62 grams of pre-melted coco fatty acid (EMERY® 626) and 0.77 grams of zinc oxide. The temperature was raised to 170° C. with good flow of nitrogen to remove the water of dilution from sodium isethionate. The reaction mixture was then raised to 240° C. in the next 60 minutes and held for two hours. During this hold period, fatty acids that escaped the reaction mass were returned to the reaction mass. Any incidental interface that had some fatty acids was not returned to the reaction mass. The distillate (water of dilution & water of reaction) collected was 155 grams against theoretical estimate of 163.52 grams. The free fatty acids (approximately 54.40 grams) were then removed from reaction mass by stripping at 240° C. in the next 60 minutes. The product, sodium cocoyl isethionate, was then discharged and flaked and had the following analysis:

Yield: 485 grams
% Free Fatty Acid (208): 12.15
% Activity (338): 78.79
pH (10%): 5.9
Gap: 9.06

In conclusion, there is a very high GAP for zinc catalyzed product where the alkalinity and pH are high.

EXAMPLE WW
(SCI Product of Invention—Viscosity Profile)
Preparation of Sodium Cocoyl Isethionate In 1000 ml. four neck round bottom flask equipped with glass stirrer, Dean Stark receiver, condenser and thermometer was added 333.69 grams of sodium isethionate (Hostapon® SI, Hoechst Celanese, % activity—57.6; alkalinity—0.25 mg KOH/g; pH—8.95) and 362.62 grams of pre-melted coco fatty acid (EMERY® R 626). The temperature was raised to 170° C. with good flow of nitrogen to remove the water of dilution from sodium isethionate. The reaction mixture was then raised to 240° C. in the next 60 minutes and held there for three hours. During this hold period, fatty acids that escaped the reaction mass were returned to the reaction mass. Any incidental interface that had some fatty acids was not returned to the reaction mass. Progress of the reaction was followed by titrating free fatty acid and anionic activity by methylene blue titration. The distillate (water of dilution & water of reaction) collected was 162.5 grams against theoretical estimate of 163.52 grams. The free fatty acids (approximately 54.40 grams) were then removed from reaction mass by stripping at 240° C. in the next 60 minutes. The product, sodium cocoyl isethionate, was then discharged and flaked and had the following analysis:

Yield: 485 grams
% Free Fatty Acid (208): 11.105
% Activity (338): 84.80
pH (10%): 4.2
Gap: 4.1

This experiment was carried out to examine the viscosity profile of the reaction mass during the whole process. Measurement of the liquid level was taken from a fixed point and at a fixed setting on the rheostat of the mixer. The levels observed at various points of the process are tabulated in TABLE XI.

EXAMPLE XX
(Acid Catalyzed SCI Product—Viscosity Profile)
Preparation of Sodium Cocoyl Isethionate In 1000 ml. four neck round bottom flask equipped with glass stirrer, Dean Stark receiver, condenser and thermometer was added 333.69 grams of sodium isethionate (Hostapon® SI, Hoechst Celanese, % activity—57.6; alkalinity—0.90 mg KOH/g; pH—12.95) and 362.62 grams of pre-melted coco fatty acid (EMERY® 626) and 0.21 grams of methane sulfonic acid. The temperature was raised to 170° C. with good flow of nitrogen to remove the water of dilution from sodium isethionate. The reaction mixture was then raised to 240° C. in the next 60 minutes and held there for three hours. During this hold period, fatty acids that escaped the reaction mass were returned to the reaction mass. Any incidental interface that had some fatty acids was not returned to the reaction mass. Progress of the reaction was followed by titrating free fatty acid and anionic activity by methylene blue titration.

The distillate (water of dilution & water of reaction) collected was 157 grams against theoretical estimate of 163.52 grams. The free fatty acids (approximately 54.40 grams) were then removed from reaction mass by stripping at 240° C. in the next 60 minutes. The product, sodium cocoyl isethionate, was then discharged and flaked and had the following analysis:

Yield: 495 grams
% Free Fatty Acid (208): 12.05
% Activity (338): 81.82
pH (10%): 4.80
Gap: 6.13

This experiment was carried out to examine the viscosity profile of the reaction mass during the whole process. Measurement of the liquid level was taken from a fixed point and at a fixed setting on the rheostat of the mixer. The levels observed at various points of the process are tabulated in TABLE XI.

EXAMPLE YY
(Zinc Catalyzed SCI Product—Viscosity Profile)
Preparation of Sodium Cocoyl Isethionate In 1000 ml. four neck round bottom flask equipped with glass stirrer, Dean Stark receiver, condenser and thermometer was added 333.69 grams of sodium isethionate (Hostapon® SI, Hoechst Celanese, % activity—57.6; alkalinity—0.90 mg KOH/g; pH—12.95) and 362.62 grams of pre-melted coco fatty acid (EMERY® 626) and 0.77 grams of zinc oxide. The temperature was raised to 170° C. with good flow of nitrogen to remove the water of dilution from sodium isethionate. The reaction mixture was then raised to 240° C. in the next 60 minutes and held there for three hours. During this hold period, fatty acids that escaped the reaction mass were returned to the reaction mass. Any incidental interface that had some fatty acids was not returned to the reaction mass. Progress of the reaction was followed by titrating free fatty acid and anionic activity by methylene blue titration.

The distillate (water of dilution & water of reaction) collected was 156 grams against theoretical estimate of 163.52 grams. The free fatty acids (approximately 54.40 grams) were then removed from reaction mass by stripping at 240° C. in the next 60 minutes. The product, sodium cocoyl isethionate, was then discharged and flaked and had the following analysis:

Yield: 490 grams
% Free Fatty Acid (208): 13.52
% Activity (338): 79.02
pH (10%): 5.2
Gap: 7.46

This experiment was carried out to examine the viscosity profile of the reaction mass during the whole process. Measurement of the liquid level was taken from a fixed point and at a fixed setting on the rheostat of the mixer. The levels observed at various points of the process are tabulated in TABLE XI.

Method of Purification of Sodium Cocoyl Isethionate

In 1000 ml. four neck round bottom flask equipped with stirrer, condenser and thermometer was added 100 grams of sodium cocoyl isethionate and 500 grams of isopropanol. The temperature was raised to 83° C. and held at 83° C. for two hours, maintaining a good reflux in the pot. The reaction mass was then cooled to 30° C. and the product filtered through Buckner funnel using Whatman paper #4. The product was rinsed with 100 grams isopropanol. Dried the wet product in the oven at 105° C. until it became bone dry. The resulting sodium cocoyl isethionate has the typical activity (308) of >95% and free fatty acid (208)<1%. This procedure was used in the purification of Example #'s CP, DP, HP, IP and JP.

| EXAMPLE NO. | SCI PRODUCT USED |
|---|---|
| CP | Example #C (SCI Product of the Invention) |
| DP | Example #D (SCI Product of the Invention) |
| HP | Example #H (TAURANOL ® 1-78 (Acid Catalyzed)) |
| IP | Example #I (TAURANOL ® 1-78E (Zinc Catalyzed)) |
| JP | Example #J (Jordapon ® Cl (Zinc Catalyzed)) |

Methods of Extraction of Anionic Actives & Gas Chromatography

In 250 ml. three neck round bottom flask equipped with stirrer, condenser and thermometer added 20 grams of purified sodium cocoyl isethionate (such as Ex. CP, DP, HP, IP, and JP, % activity (338)>95;% free fatty acid (208)<1.0), 80 grams of deionized water and 10 grams of 50% potassium hydroxide solution. The temperature was raised to 45° C. and held for 60 minutes. Top layer of reaction mass was pasty dispersion (pH approximately 14). Adjusted the pH to approximately 5.0 and the top layer became clear. Top layer was transferred to a beaker and converted into methyl esters using universal methyl ester method. The resulting methyl esters were analyzed by gas chromatography. This method was used in determining the C-chain distributions of the anionic SCI product by excluding the free fatty acids from its parent SCI product. The exclusion of free fatty acids was done by the previously mentioned purification (extraction) method.

Analytical Results

Tables II-A and II-B below show the esters of the invention (i.e., compounds C., D and E) have much smaller GAPs than the commercial/trade products and the exemplified catalyzed reaction products A, B, F, G, H and I. The GAP is defined as:

GAP=100−(ACTIVITY+FFA)

Stated otherwise,

GAP=NIS+Inorganic matter+any analytical deviational #.

The GAP represents unaccounted material (other than the reactants and reacted material) which is undesirable in the SCI products of the prior art as it is responsible for skin and eye irritation and the presence of soap. The esters of the invention have far less unknowns or unaccounted material and, accordingly, much less disproportionation of the C-chain distribution of the anionic surfactant SCI product formed.

Additionally, the absence or negligible presence of alkalinity in the esters of the invention (compounds C, D, & E) indicates the absence or negligible presence of soap-like species in the esters of the invention. Soap-like species are known to cause skin and eye irritation. The absence or negligible presence of soap-like species is an advantageous property of SCI products which are used mainly in formulating personal care products such as skin and hair care products.

TABLE II-A

ANALYTICAL RESULTS USING STANDARD (ASSIGNED) MOLECULAR WEIGHTS

| SCI Product I.D. | Activity %[1] | FFA %[2] | GAP %[3] | ALKALINITY mgm KOH/g. | pH 10% Solution |
|---|---|---|---|---|---|
| EX. A | 82.28 | 10.23 | 7.49 | 0.88 | 5.31 |
| EX. B | 83.84 | 9.50 | 6.66 | 2.72 | 5.75 |
| EX. C | 83.76 | 12.17 | 4.07 | 0.25 | 5.25 |
| EX. D | 84.87 | 10.84 | 4.29 | 0.22 | 5.00 |
| EX. E | 84.88 | 12.14 | 2.98 | 0.20 | 4.30 |
| EX. F | 80.32 | 11.12 | 8.56 | 2.02 | 4.80 |
| EX. G | 78.95 | 12.05 | 9.00 | 3.80 | 5.10 |
| EX. H | 82.97 | 8.97 | 8.06 | 1.13 | 5.35 |
| EX. I | 82.03 | 9.70 | 8.27 | 3.50 | 5.80 |

[1]Mol. Wt. = 338
[2]Mol. Wt. = 208
[3]GAP = 100 − (Activity + FFA)

TABLE II-B

ANALYTICAL RESULTS USING ACTUAL (FOUND BY ANALYSIS) MOLECULAR WEIGHTS

| SCI Product I.D. | Activity (Act.) % | Activity (mol. wt.) found | FFA % | FFA (mol. wt) found | GAP = 100 − (Act. + FFA) |
|---|---|---|---|---|---|
| EX. A | 83.93 | 345 | 10.57 | 215 | 5.50 |
| EX. B | 85.52 | 345 | 9.81 | 215 | 4.67 |
| EX. C | 84.26 | 340 | 13.64 | 219 | 2.10 |
| EX. D | 85.87 | 342 | 11.31 | 217 | 2.80 |
| EX. E | 85.89 | 342 | 12.29 | 214 | 1.62 |
| EX. F | 81.34 | 345 | 12.15 | 215 | 6.51 |
| EX. G | 79.97 | 345 | 13.08 | 215 | 6.95 |
| EX. H | 83.98 | 343 | 9.36 | 217 | 6.66 |
| EX. I | 83.05 | 345 | 10.74 | 217 | 6.21 |

For examples C, D & E, which are products of the invention, the GAPs are extremely low.

Carbon Chain Distribution/Comparative Gas Chromatography Analysis of the Anionic Active Surfactant Molecule, Free Fatty Acids vs. starting Fatty Acids As demonstrated in Table III, there is less disproportionation, i.e., change in the carbon-chain distribution, for the products of the invention (Compounds C., D & E) as compared to commercially available SCI products (Compounds H, I & J). The commercially available, catalyzed products H, I, and J show the C-chain distribution having changed from that of the starting fatty acids. This change in the C-chain distribution results in or is manifested by an increase in the molecular weight of the anionic active surfactant molecule. Molecular weight disproportionation is shown in Table IV.

In contrast, the C-chain distribution is minimally changed in the case of the esters of the invention (C, D & E). Thus, the analysis of the esters of the invention is based on the true molecular weight derived from the starting fatty acids rather than on any other higher disproportioned molecular weights as generated in the SCI products of the catalyzed reactions.

Table IV depicts the analysis results reported based on adjusted/equalized molecular weights (from analysis). By disproportionation is meant the deviations from the starting molecular weights and the molecular weights found by analysis. Even with the use of higher adjusted (from analysis) molecular weights for the products of the catalyzed reactions, there is still a GAP between 100% and the total of Activity and FFA reflecting that other species such as soap and unreacted sodium isethionate are present in much greater proportions than in the products of the invention. The GAP is much smaller in the esters of the invention than in the products of the catalyzed reactions.

In-Process Analysis for Conversions at Various Intercepts

Tables V and VI compare an ester of the invention (E) against an acid catalyzed ester (F) and a zinc catalyzed ester (G). Table V shows the activities actually formed on an "as is" basis. The results indicated higher conversion at every intercept of the in-process analysis demonstrating that the ester of the invention is superior to its catalyzed counterparts.

Table VI shows the relative percentage conversion of the product of the invention vs. that of the known catalyzed esters. For this comparison, the % Activity of 84.88 formed in the product of the invention is assigned to be 100 and the found activities of the catalyzed products are factored upwards, i.e., multiplied by a factor: 100/84.88=1.178. This upward factoring equalizes the percentage relationship of the three products on a uniform basis. The comparison shows the shortage of the Activity Formation, i.e., conversions in the case of catalyzed reaction products on the basis of equalized results.

The GAP column in Table V shows a rapid drop in the residual GAP as the progress of the reaction continues to form relatively higher Activity in the case of the products of the invention as compared to the products of the catalyzed reaction products.

The SCI product of the invention (Ex. D=pH 4.3) generally has the same or a lower pH than the acid catalyzed SCI

TABLE III

C-CHAIN DISTRIBUTION/COMPARATIVE GAS CHROMATOGRAPHY ANALYSIS
(% COMPOSITIONS)

| Fatty Acid | Fatty Acid | SCI Product | Starting Coco | SCI Product C | | SCI Product D | | SCI Product E | |
|---|---|---|---|---|---|---|---|---|---|
| C-Chain # | mol. wt. | Formed[1] (mol. wt.) | Fatty Acids | Anionic Formed | FFA Residual[2] | Anionic Formed | FFA Residual | Anionic Formed | FFA Residual |
| C8 | 144 | 274 | 5.64 | 4.98 | 2.92 | 5.10 | 4.27 | 5.10 | 4.37 |
| C10 | 172 | 302 | 5.52 | 5.48 | 3.14 | 5.40 | 3.56 | 5.30 | 4.13 |
| C12 | 200 | 330 | 53.80 | 53.66 | 50.00 | 53.66 | 50.36 | 53.20 | 51.56 |
| C14 | 228 | 358 | 18.95 | 19.46 | 22.54 | 19.44 | 21.67 | 19.65 | 19.70 |
| C16 | 256 | 386 | 8.27 | 8.44 | 11.21 | 8.66 | 10.47 | 9.20 | 10.27 |
| C18 | 284 | 414 | 7.80 | 7.36 | 10.18 | 7.73 | 9.63 | 7.49 | 9.33 |
| Total | | | 100 | 100 | 100 | 100 | 100 | 100 | 100 |
| Mol. Wt. (Found) | | | 212[3] | 340 | 219 | 342 | 217 | 342 | 214 |
| Mol. Wt. (Calculated) | | | 212 | 340 | 212 | 340 | 212 | 340 | 212 |

| | Fatty Acid | SCI Product H | | SCI Product I | | SCI Product J | |
|---|---|---|---|---|---|---|---|
| | C-Chain # | Anionic Formed | FFA Residual | Anionic Formed | FFA Residual | Anionic Formed | FFA Residual |
| | C8 | 5.47 | 3.12 | 3.92 | 3.01 | 4.62 | 7.36 |
| | C10 | 5.24 | 4.21 | 4.26 | 3.72 | 4.98 | 5.43 |
| | C12 | 52.23 | 50.42 | 53.25 | 52.67 | 51.54 | 52.28 |
| | C14 | 19.65 | 21.24 | 21.71 | 20.57 | 19.98 | 18.81 |
| | C16 | 10.54 | 10.31 | 8.53 | 10.22 | 9.46 | 8.30 |
| | C18 | 6.84 | 10.18 | 8.30 | 9.78 | 9.38 | 7.49 |
| | Total | 100 | 100 | 100 | 100 | 100 | 100 |
| | Mol. Wt. (Found) | 343 | 217 | 345 | 217 | 345 | 210 |
| | Mol. Wt. (Calculated) | 338 | 208 | 338 | 208 | 338 | 208 |

[1]By SCI Product Formed is meant anionic activity of the SCI Product Formed.
[2]By FFA Residual is meant unreacted, residual FFA.
[3]Molecular weight may vary between 208–212. The molecular weight of 212 is the actual found mol. wt. by titration with sodium hydroxide.

product (Ex. F=pH 4.8) and a significantly lower pH than the zinc catalyzed SCI product (Ex. G=pH 5.1). The zinc catalyzed product forms a salt in reaction.

Table V-A is derived from TABLE V and compares the mole ratios used as initial mole ratios of NIS to CFA (Coco Fatty Acids) and in-process ratios of the process of the invention vs. the prior art catalyzed product processes. As shown in TABLE V-A, higher conversion at all intercepts demonstrates the shorter processing times and superior color and odor stability for the SCI product of the invention as compared to prior art SCI products.

Table V-B is a condensed format derived from the Table V-A. Table V-B reflects on the intrinsically increased ratio of CFA to NIS in-process as compared to catalyzed reactions. The ratio is increased intrinsically because it is occurring without any refurbishment at all. Such phenomenon is the result of the process of the invention which allows, without deliberate refurbishment of fatty acids, a high ratio of fatty acids to NIS. This aspect permits high conversions and hence lower unknowns as GAP (referred to in Tables II-A, II-B, AND V).

TABLE IV

MOLECULAR WEIGHTS FOUND & DEVIATIONS (DISPROPORTIONATION)

| | SCI PRODUCT C | | SCI PRODUCT D | | SCI PRODUCT E | | SCI PRODUCT H | | SCI PRODUCT I | | SCI PRODUCT J[7] | |
|---|---|---|---|---|---|---|---|---|---|---|---|---|
| | Anionic Formed[3] | FFA Residual[4] | Anionic Formed | FFA Residual | Anionic Formed | FFA Residual | Anionic Formed | FFA Residual | Anionic Formed | FFA Residual | Anionic Formed | FFA Residual |
| Mol. Wt. Found[1] | 340 | 219 | 342 | 217 | 342 | 214 | 343 | 217 | 345 | 217 | 345 | 210 |
| Mol. Wt. Assigned[2] | 342 | 212 | 342 | 212 | 342 | 212 | 338 | 208 | 338 | 208 | 338 | 208 |
| Difference | −2 | 7 | 0 | 5 | 0 | 2 | 5 | 9 | 7 | 9 | 7 | 2 |
| % CHANGE/ DEVIATION | | | | | | | | | | | | |
| ANIONIC: | | | | | | | | | | | | |
| @338[5] | | | | | | | 1.48 | | 2.07 | | 2.07 | |
| @342[6] | −0.59 | | 0 | | 0 | | — | | — | | — | |
| FFA: | | | | | | | | | | | | |
| @208[5] | | | | | | | | 4.32 | | 4.32 | | 0.96 |
| @212[6] | | 3.30 | | 2.36 | | 0.94 | | — | | — | | — |

[1]Starting Fatty Acid:
mol. wt. found = 212
mol. wt. assigned (calculated from analysis) = 212
Difference = 0
[2]By "Mol. Wt. Assigned" is meant the Mol. Wt. calculated from analysis.
[3]By "Anionic Formed" is meant SCI Product Formed.
[4]By "FFA Residual" is meant unreacted, residual FFA.
[5]Assigned standard mol. wts.
[6]Actually found mol. wts. in the Anionic Formed and Residual FAA, found by Gas Chromatography.
[7]The product analysis of SCI-Product J (Jordapon CI) was performed on an actual sample from the trade.

TABLE V

CONVERSION: IN PROCESS ANALYSIS/FINAL ANALYSIS

| | SCI-Product E | | | | SCI-Product F | | | | SCI-Product G | | | |
|---|---|---|---|---|---|---|---|---|---|---|---|---|
| | A SCI Product Formed[1] (as is basis) % | B FFA (FFA) % | C GAP = 100 − (a + b) % | D Alkalinity mgm KOH/gm & pH 10% % | A SCI Product Formed (as is basis) % | B FFA (FFA) % | C GAP = 100 − (a + b) % | D Alkalinity mgm KOH/gm & pH 10% % | A SCI Product Formed (as is basis) % | B FFA (FFA) % | C GAP = 100 − (a + b) % | D Alkalinity mgm KOH/gm & pH 10% % |
| Initial @ 140° C. | | 69.70 | | | | 68.96 | | | | 68.96 | | |
| Initial @ 240° C. | | 59.32 | | | | 59.32 | | | | 57.80 | | |
| 1 Hr. @ 240° C. | 16.30 | 51.90 | 31.80 | | 12.20 | 54.87 | 29.92 | | 10.10 | 55.61 | 34.29 | |
| 2 Hrs. @ 240° C. | 60.10 | 30.40 | 9.50 | | 47.88 | 36.33 | 15.79 | | 42.10 | 40.41 | 17.49 | |
| 3 Hrs. @ 240° C. | 68.30 | 25.95 | 5.75 | | 62.10 | 28.92 | 8.98 | | 58.80 | 32.62 | 8.58 | |
| 4 Hrs. @ 240° C. | 84.88 | 12.14 | 2.98 | 0.23/4.30 | 80.32 | 11.12 | 8.56 | 2.02/4.8 | 78.95 | 12.05 | 9.00 | 5.30/5.1 |

[1]By "SCI Product Formed" is meant the activity formed on an "as is" basis.

TABLE V-A (Data based on Table V)

CONVERSION & MOLE RATIO RELATIONSHIP

|  | SCI Product: E | | | | SCI Product: F | | | | SCI Product: G | | | |
|---|---|---|---|---|---|---|---|---|---|---|---|---|
|  | % | | Moles | | % | | Moles | | % | | Moles | |
|  | NIS | FFA | NIS | FFA | NIS | FFA | NIS | FFA | NIS | FFA | NIS | FFA |
| Initial Dry Charge | 35 | 65 | 0.2365 | 0.3066 | 35 | 65 | 0.2365 | 0.3125 | 35 | 65 | 0.2365 | 0.3125 |
| Initial Mole Ratio |  |  | 1.00 | 1.3214 |  |  | 1.00 | 1.3214 |  |  | 1.00 | 1.3214 |
| Starting Molecular Wts. | 148 | 208 |  |  | 148 | 208 |  |  | 148 | 208 |  |  |
| Found Molecular Wts. (Product Mixture of Reaction) |  | 212 |  |  |  | 217 |  |  |  | 217 |  |  |
| 1 Hr. Reaction: Activity Found | (16.30%) | | | | (12.20%) | | | | (10.10%) | | | |
| Consumed by Activity | 7.13 | 10.22 |  |  | 5.34 | 7.65 |  |  | 4.42 | 6.33 |  |  |
| Residual Calculated | 27.87 | 54.88 | 0.1883 | 0.2644 | 29.66 | 57.35 | 0.2004 | 0.2705 | 30.58 | 58.67 | 0.2066 | 0.2767 |
| Residual Balance Found |  | 51.90 |  | 0.2448 |  | 54.87 |  | 0.2588 |  | 55.61 |  | 0.2623 |
| Residual Mole Ratio Calculated |  |  | 1.00 | 1.4041 |  |  | 1.000 | 1.3498 |  |  | 1.000 | 1.3393 |
| Residual Mole Ratio Found |  |  | 1.00 | 1.3000 |  |  | 1.000 | 1.2914 |  |  | 1.000 | 1.2696 |
| 2 Hr. Reaction: Activity Found | (60.10%) | | | | (47.88%) | | | | (42.10%) | | | |
| Consumed by Activity | 26.32 | 37.70 |  |  | 20.97 | 30.03 |  |  | 18.43 | 26.41 |  |  |
| Residual Calculated | 8.68 | 27.30 | 0.05865 | 0.1288 | 14.03 | 34.97 | 0.0948 | 0.1650 | 16.57 | 38.59 | 0.1120 | 0.1820 |
| Residual Balance Found |  | 30.40 |  | 0.1434 |  | 36.33 |  | 0.1714 |  | 40.41 |  | 0.1906 |
| Residual Mole Ratio Calculated |  |  | 1.000 | 2.1956 |  |  | 1.000 | 1.7405 |  |  | 1.000 | 1.6250 |
| Residual Mole Ratio Found |  |  | 1.000 | 2.4437 |  |  | 1.000 | 1.808 |  |  | 1.000 | 1.7018 |
| 3 Hr. Reaction: Activity Found | (68.30%) | | | | (62.10%) | | | | (58.80%) | | | |
| Consumed by Activity | 29.91 | 42.84 |  |  | 27.19 | 38.95 |  |  | 25.75 | 36.88 |  |  |
| Residual Calculated | 5.09 | 22.16 | 0.0344 | 0.1045 | 7.81 | 26.05 | 0.0528 | 0.1229 | 9.25 | 28.12 | 0.0625 | 0.1326 |
| Residual Balance Found |  | 25.95 |  | 0.1224 |  | 28.92 |  | 0.1364 |  | 32.62 |  | 0.1539 |
| Residual Mole Ratio Calculated |  |  | 1.000 | 3.038 |  |  | 1.000 | 2.3276 |  |  | 1.000 | 2.1216 |
| Residual Mole Ratio Found |  |  | 1.000 | 3.558 |  |  | 1.000 | 2.5833 |  |  | 1.000 | 2.4624 |
| 4 Hr. Reaction: Activity Found | (84.88%) | | | | (80.32%) | | | | (78.95%) | | | |
| Consumed by Activity | 37.16 | 53.24 |  |  | 35.17 | 50.38 |  |  | 34.57 | 49.52 |  |  |
| Residual Calculated | −2.16 | 11.76 | 0 | 0.05547 | −0.17 | 14.62 | 0 | 0.0689 | 0.43 | 15.48 | 0.0030 | 0.0730 |
| Residual Balance Found |  |  |  | 0.05726 |  | 11.12 |  | 0.05245 |  | 12.05 |  | 0.05684 |

Molecular Wts. used for calculation on Product Mixtures:    NIS = 148    FFA = 212    Activity = 338
NIS = Sodium Isethionate    FFA = Free Fatty Acids    Activity = SCI-Product

TABLE V-B

MOLE RATIO RELATIONSHIP
NIS @ 1.0 MOLE:FFA @ VARIABLE

|  |  | REACTION TIMES | | | | |
|---|---|---|---|---|---|---|
| SCI PRODUCTS: |  | INITIAL | 1 HR. | 2 HR. | 3 HR. | 4 HR. |
| $E_1$ % | ACTIVITY FORMED | 0 | 16.30 | 60.10 | 68.30 | 84.88 |
| Molar Ratio | CALCULATED | 1.3214 | 1.4041 | 2.1956 | 3.036 |  |
| Molar Ratio | FOUND |  | 1.3000 | 2.4437 | 3.558 |  |
| Ratio Greater than Initial | % | As 100 | −1.60 | 84.98 | 169.26 |  |
| F % | ACTIVITY FORMED | 0 | 12.20 | 47.88 | 62.10 | 80.32 |
| Molar Ratio | CALCULATED | 1.3214 | 1.3498 | 1.7405 | 2.3276 |  |
| Molar Ratio | FOUND |  | 1.2914 | 1.8080 | 2.5833 |  |
| Ratio Greater than Initial | % | As 100 | −2.60 | 36.82 | 95.50 |  |
| G % | ACTIVITY FORMED | 0 | 10.10 | 42.10 | 58.80 | 78.95 |
| Molar Ratio | CALCULATED | 1.3214 | 1.3393 | 1.6250 | 2.1216 |  |
| Molar Ratio | FOUND |  | 1.2696 | 1.7018 | 2.4624 |  |
| Ratio Greater than Initial | % | As 100 | −3.92 | 28.79 | 86.35 |  |

[1] E is a product of the invention; F is an acid catalyzed product and G is a zinc catalyzed product.

The process of this invention uses the same starting ratio of NIS to coco fatty acids (CFA) as the other acid catalyzed or zinc catalyzed reactions. However during the course of the reaction, i.e., in-process, the ratio of NIS to free fatty acids in the case of the invention is consistently maintained, on its own, higher than the starting ratio. The increased ratio of NIS to FFA is approximately 84.98% greater than its starting ratio at a 2 hr. interval and 169% greater than its starting ratio at a 3 hr. interval. The increase of NIS to FFA in the case of an acid catalyzed reaction (Ex. Nos. F. & H) is a meager 36.8% at 2 hr. and 95.5% at 3 hr. interval. The increase of NIS to FFA in the case of the zinc catalyzed reaction (Ex. Nos. G & I) is also a meager 28.79% at 2 hr. and 86.35% at 3 hr. interval.

This feature of a higher ratio of NIS to FFA, especially during the entire reflux period and before the stripping cycle, is achieved in the process of the invention despite the same starting ratios of the same raw materials.

Residual Final Alkalinity and pH (Shown in Table V)

The alkalinity of the zinc catalyzed product is almost 25-fold higher than the alkalinity of the ester of the invention while that of acid catalyzed product is almost 10-fold higher. The pH of the ester of the invention is closer to that of a pure product without any impurities contrary to that of the catalyzed products which reflects the presence of non-active extraneous materials such as soap/unreacted sodium isethionate/inorganic matter, etc.

no more than 92.22%. The alkalinity/soap is also greater in the case of the acid and zinc catalyzed products as compared to the products of the invention. Product JP (a commercially available zinc catalyzed product) shows even worse analytical results, i.e., activity is only 91.26%, FFA is 0.83% and soap is 2.87%, reflecting its high alkalinity of 7.01 mgm KOH/gm.

Thus, the process of the invention reaches a greater state of activity, or a higher reaction rate, which is an indication of the completeness of the reaction. This feature advantageously makes the process economical, and provides a product of good color and stability. Lower GAP of analysis is indicative of better stability. See individual examples of invention and related Tables.

Formulation Benefit in a Clear/Mild Conditioning Shampoo A

TABLE VI

RELATIVE COMPARISON OF CONVERSION

| | SCI-Product E | | | SCI-Product F | | | SCI-Product G | | |
|---|---|---|---|---|---|---|---|---|---|
| Intercept @ Reaction Temps | A Activity Formed[1] % | B** Activity Equalized % | C Activity Shortage % | D Activity Formed % | E Activity Equalized % | F Activity Shortage[2] % | G Activity Formed % | H Activity Equalized % | J Activity Shortage[3] % |
| 1 Hr. | 16.30 | 19.20 | | 12.20 | 14.37 | 4.83 | 10.10 | 11.90 | 7.30 |
| 2 Hrs. | 60.10 | 70.80 | | 47.88 | 56.40 | 14.40 | 42.10 | 49.59 | 21.21 |
| 3 Hrs. | 68.30 | 80.46 | | 62.10 | 73.15 | 7.31 | 58.80 | 69.27 | 11.19 |
| 4 Hrs. (Final) | 84.88 | 100.00 | None | 80.32 | 94.85 | 5.15 | 78.95 | 93.00 | 7.00 |

**Columns B, E and H are equalized to final activity of SCI-Product E, i.e., 84.88% activity of SCI-Product E is equalized to 100% and the same factor is applied to columns E & H.
Conversion factor for columns (A to B), (E to F) and (H to J) is = 1.178.
[1]By "Activity Formed" is meant the rate of conversion.
[2]F, Activity Shortage is = B – E, or the gap of B minus E, expressed as –Ve.
[3]J, Activity Shortage is = B – H, or the gap of B minus H, expressed as –Ve.

Purified SCI-Products for Analytical Measurements of Impurities/GAP

The SCI product as an active ingredient is insoluble in isopropanol (IPA), as are impurities such as unreacted sodium isethionate and incidental inorganic matter. Unreacted coconut fatty acid is completely soluble in IPA. Purifications were carried out by refluxing SCI-products and the IPA-solubles such as free fatty acid were removed by filtration and washing with additional Isopropanol to the extent that the residual free fatty acid was less than 1% as a minimum requirement. The analysis of such purified SCI products is shown in Table VII.

TABLE VII

PURIFIED SCI-PRODUCT/ANALYSIS

| SCI Product I.D.[1] | Activity %[2] | FFA %[3] | Soap %[4] | Alkalinity mgm KOH/g | GAP % |
|---|---|---|---|---|---|
| CP | 95.80 | 1.1 | 0.12 | 0.30 | 2.98 |
| DP | 96.03 | 0.95 | 0.16 | 0.40 | 2.86 |
| HP | 92.07 | 0.98 | 1.44 | 3.50 | 5.36 |
| IP | 92.22 | 0.98 | 1.44 | 3.50 | 5.36 |
| JP | 91.26 | 0.83 | 2.87 | 7.01 | 5.03 |

[1]By CP, DP, HP, IP and JP is meant the purified forms of SCI products C, D, H, I and J identified in Table I above.
[2]Molecular weight 338.
[3]Molecular weight 208.
[4]Molecular weight 230.

The esters of the invention give less than 3% GAP and Activity of greater than 95% while the acid and zinc catalyzed products give greater than 5% GAP and activity of The following is a representative formulation for conditioning shampoo "A". Table VIII gives the results of viscosity tests. Products A and B show much lower viscosity than product D which is the product of the invention.

TABLE VIII

CLEAR & MILD CONDITIONING SHAMPOO "A"

FORMULATIONS: (IN GRAMS)

| SCI Product I.D. | FORMULATION A | FORMULATION B | FORMULATION C |
|---|---|---|---|
| EX. A (TAURANOL ® I-78) | 6 | — | — |
| EX. B (TAURANOL ® I-78-E) | — | 6 | — |
| EX. D (SCI-INVENTION) | — | — | 6 |
| AMMONIUM LAURYL SULFATE | 15 | 15 | 15 |
| FINQUAT ® CT | 5.0 | 5.0 | 5.0 |
| AMINOL ® HCA | 5.0 | 5.0 | 5.0 |
| WATER | 69 | 69 | 69 |
| TOTAL | 100 | 100 | 100 |
| VISCOSITY (cps) at 25° C. | 240 | 260 | 1580 |

FINQUAT ®, AMINOL ® and TAURANOL ® are registered trademarks of Finetex, Inc., Elmwood Park, New Jersey.

Formulation Benefits in a Clear and Mild Cleansing Gel

The following is a representative formulation for a cleansing gel. Table IX gives the results of viscosity tests. The acid catalyzed product A shows lower viscosity than the zinc catalyzed product B and the product D which is the product of the invention. The formula specific effects on viscosity are realized in this formulation where the product of the invention process compares very well with that of the zinc catalyzed product without losing any viscosity profile of the formulation. The product of the invention process delivers a composition with less impurities such as soap/alkaline materials which are known in the industry to cause eye/skin irritation.

TABLE IX

CLEAR & MILD SKIN CLEANSING GEL

| SCI Product I.D. | FORMULATION A | FORMULATION B | FORMULATION C |
|---|---|---|---|
| | FORMULATIONS: (IN GRAMS) | | |
| EX. A (TAURANOL ® I-78) | 6 | — | — |
| EX. B (TAURANOL ® I-78-E) | — | 6 | — |
| EX. D (SCI-INVENTION) | — | — | 6 |
| AMMONIUM LAURETH-2 SULFATE | 15 | 15 | 15 |
| COCOBETAINE | 6 | 6 | 6 |
| POLYOL ALKOXY ETHER (CROTHIX ®) | 2 | 2 | 2 |
| WATER | 70.5 | 70.5 | 70.5 |
| PRESERVATIVE | 0.5 | 0.5 | 0.5 |
| TOTAL | 100 | 100 | 100 |
| VISCOSITY (cps) at 25° C. | 3700 | 7350 | 7400 |

TAURANOL ® is a registered trademark of Finetex, Inc., Elmwood Park, New Jersey. CROTHIX ® is a registered trademark of Croda, Inc. Parsippany, New Jersey.

Soap-Free SCI Products

The SCI products of the invention are free of soap and may be used in clear liquid formulations whereas prior art SCI products show limited solubility in water which restricts their use to soaps and opaque liquid formulations.

The SCI products of the invention have different solubilities than prior art SCI products. The freshly prepared solutions of 5–7 grs./ltr. strength in deionized water show that the solutions of the prior art SCI products are slightly to highly hazy at 25° C. whereas the solutions of the SCI products of the invention are sparkling clear. This indicates the absence of soap-like species in the products of this invention and as such, these products are true syndet materials free of soap.

Foam Generation

Table X shows that the presence of soap reduces foam. For deionized water (XA) and hard water (XB), FAA=less than 1%. Table X-A is for test run in 0 ppm hardness (deionized water). The product of the invention, i.e., SCI product Example C., gives a comparable foam to that: of the acid catalyzed product of Example A. The SCI product B (zinc catalyzed) gives slightly lower foam. A slightly lower concentration of 0.166% of Example C and the same with addition of 0.066% Soap (sodium soap of coco fatty acids) was tested for foam. This showed that the presence of soap in such SCI products hampers the foaming characteristics. Example B shows such behavior of lower foaming. Example D (a product of the invention) gives a higher foam then Example B even at a lower concentration of 0.166%. This is a significant difference in concentration giving the same or slightly better foam heights, as 0.166% is only 83% of 0.2% concentration of Example B. Example C also shows a close comparison in foam height to Example A (acid catalyzed).

Foam Heights in Hard Water

Table X-B shows foam test done in hard water of 300 ppm hardness. A purified version of Example # CP (a purified version of Example C) was tested for foam heights vs. the other examples. The purified example had Activity of >95% and FFA@<1%. Table X-B shows that Examples C. and D (both products of the invention) give foam heights nearly close to or higher than purified products. Examples A and B (the catalyzed products) show much lower foam heights. This effect and property offered by the products of the invention is advantageous in the industry where higher foaming effects in hard water are beneficial especially in facial cleansers, hair and skin care product formulations.

TABLE X-A

FOAM TEST (ROSS-MILES) AT 50° C.; WATER HARDNESS = 0 ppm

| | Concentration | Foam Height (mm) | |
|---|---|---|---|
| SCI Product I.D. | % | Initial | 5 Min |
| EX. A | 0.20 | 150 | 150 |
| EX. B | 0.20 | 145 | 145 |
| EX. C | 0.20 | 150 | 150 |
| EX. D | 0.20 | 150 | 150 |
| EX. D | 0.166 | 148 | 148 |
| EX. C + | 0.20 | 110 | 110 |
| Soap % | 0.066 | | |
| EX. C | 0.166 | 148 | 148 |

TABLE X-B

FOAM TEST (ROSS-MILES) @ 50° C.; WATER HARDNESS = 300 ppm

| | Concentration | Foam Height (mm) | |
|---|---|---|---|
| SCI Product I.D. | % | Initial | 5 Min |
| EX. A | 0.2 | 160 | 160 |
| EX. B | 0.2 | 160 | 160 |
| EX. C | 0.2 | 165 | 165 |
| EX. D | 0.2 | 170 | 170 |
| EX. E Pure | 0.2 | 168 | 168 |
| FFA | <1% | | |

The return of FFA is a viscosity lowering factor during the process of the invention. The viscosity of the products of the invention is controlled, i.e., kept low, by returning the FFA, which keeps the acids high and keeps the reaction fluid. Fat and water of reaction is azeotroped, water is removed and FFA are returned. Thus, returning the FFA results in increased fluidity and lower viscosity of the reactants, which allows for improved mixing of the reactants during the reaction and better, more uniform heat distribution.

The products of the SCT are relatively viscous even in the high temperatures of the reactor. Increased viscosity produces poor heat dissipation and poor mixing of the materials during the reaction. These factors result in an uneven product which can often be burned or is otherwise unsatisfactory. These problems do not occur in or affect: the products of the invention.

TABLE XI

VISCOSITY PROFILES IN-PROCESS at DIFFERENT INTERCEPTS

| | Example Numbers ||||||||| 
| | SCI Product of Invention Ex. #WW ||| SCI Product Acid Catalyzed Ex. #XX ||| SCI Product Zinc Catalyzed Ex. #YY |||
| Levels in Centimeters | Without Mixing | With Mixing | Difference in Level | Without Mixing | With Mixing | Difference in Level | Without Mixing | With Mixing | Difference in Level |
|---|---|---|---|---|---|---|---|---|---|
| Initial Level | 11.00 | 9.50 | 1.50 | 11.00 | 9.50 | 1.50 | 11.00 | 9.50 | 1.50 |
| 1 Hr. in Vessel (Water of Diluting Out) | 10.90 | 9.50 | 1.40 | 10.90 | 9.50 | 1.40 | 10.90 | 9.50 | 1.40 |
| 2 Hrs. in Vessel (Reached Reaction Temp. 240° C.) | 10.70 | 9.30 | 1.40 | 10.70 | 9.40 | 1.35 | 10.70 | 9.40 | 1.30 |
| Hold Periods @ 240° C.: | | | | | | | | | |
| 1 Hr. Hold @ 240° C. | 10.70 | 9.30 | 1.40 | 10.65 | 9.35 | 1.30 | 10.60 | 9.40 | 1.20 |
| 2 Hrs. Hold @ 240° C. | 10.70 | 9.35 | 1.35 | 10.65 | 9.40 | 1.25 | 10.60 | 9.55 | 1.05 |
| 3 Hrs. Hold @ 240° C. | 10.70 | 9.40 | 1.30 | 10.65 | 9.55 | 1.10 | 10.60 | 9.70 | 0.90 |
| 4 Hrs. Hold @ 240° C. | 10.70 | 9.50 | 1.25 | 10.60 | 9.70 | 0.90 | 10.60 | 9.85 | 0.75 |

Note:
Greater the difference in levels, thinner the product
Lower the difference in levels, thicker (more viscous) the product Viscosity of Mixture In-Process The product of the invention offers an in-process mixture of relatively lower viscosity than the acid-catalyzed or zinc-catalyzed product mixtures. This is tabulated in TABLE XI. A drop in the level was measured during the reaction process times. The mixing speed was maintained at constant setting of the rheostat for the mixer. The higher drop in the level of the mixture indicates a more viscous mixture. The lower drop in level indicates the formation of a vortex which indicates a thinner mixture. The measurements were done from a fixed point of the same glass vessel i.e. round bottom flask, used for the reactions.

The reaction mass being very hot, and to keep the integrity of the mass under inert atmosphere, the levels of the respective reaction mixtures were measured from outside of the glass vessel. Viscosity measurements are very difficult (or next to impossible) to measure in-process by the use of a viscometer spindle without introducing errors in measurements which would distort examination of this property for comparative purposes.

The sodium cocoyl isethionate of the invention has the following properties:

| | |
|---|---|
| appearance: | white to off-white flakes or chips or powder or noodles; |
| active content, %: | 80–90 |
| pH, 10% solution at 35° C.: | 4.0–6.0 |
| moisture, %: | 0.5 maximum |
| free fatty acid, %: | 7–16 |
| color, APHA, 5% in 30% n-propanol 70% distilled water (ASTM-D-1209-79) | 50 maximum |

By "Active content" is meant the same as Activity, i.e., SCI product.

It is understood that the embodiments described herein are merely exemplary and that a person skilled in the art may make many variations and modifications without departing from the spirit and scope of the invention. All such modifications and variations are intended to be included within the scope of the invention described herein.

What is claimed is:

1. In a process wherein fatty acids are reacted with hydroxyalkyl sulfonic acid salt to yield a corresponding isethionate fatty acid ester, the steps comprising:

(a) mixing together and heating in a reaction vessel a molar excess of fatty acids of formula (I):

RCOOH     (I)

containing from 8 to 24 carbon atoms, with a 2-hydroxyalkyl sulfonic acid salt of formula (II):

HOR$^1$SO$_3$X     (II)

wherein R$^1$ is a saturated or unsaturated straight chain C2–C4 hydrocarbyl group selected from the group consisting of ethylene, propylene and butylene;
and X is selected from the group consisting of sodium, potassium, lithium, ammonium, calcium, magnesium, barium, amines, and triethanol amines;
in the absence of sufficient acid or alkaline agents to catalyze the reaction;

(b) returning all distillate fatty acids to the reaction vessel;

(c) allowing the reaction to proceed substantially toward completion under conditions sufficient to maintain the fluidity of the reaction mixture while continuously removing water from the reaction mixture, until no further condensation can be achieved in the reaction vessel;

(d) discontinuing return of the distillate fatty acids and progressively reducing the pressure in the reaction vessel containing said reaction mass while maintaining the fluidity of the reaction mixture;

(e) distilling off free, unreacted fatty acids from the reaction mass by stripping at a temperature in the range of 200° C. to 250° C.; and (f) releasing the vacuum, discharging and flaking the isethionate fatty acid ester so formed.

2. The process of claim 1 wherein the alkalinity of the sulfonic acid salt is not more than 1.5 mgms KOH/gm, and the acidity of the sulfonic acid salt is not more than 1.0 mgms KOH/gm.

3. The process of claim 1 wherein the molar ratio of sulfonic acid salt to fatty acids ranges from a maximum of 1:1.5 to a minimum of 1:1.1.

4. The process of claim 1 wherein step (a) is carried out in the presence of an inert atmosphere at temperatures ranging between 200° C. and 250° C.

5. The process of claim 1 wherein the 2-hydroxyalkyl sulfonic acid salt used in step (a) is introduced in the form of an aqueous solution.

6. The process of claim 1 wherein in step (b) distillate fatty acids are returned to the reaction vessel in a ratio of 15 parts of distillate fatty acids to 85 parts of starting fatty acids.

7. The process of claim 1 wherein in step (c) the reaction proceeds until the free fatty acid content of the reaction mass in the reaction vessel is in the range of 15 wt % to 18 wt. %.

8. The process of claim 1 wherein in step (d) the pressure is reduced in the range of from 5 inches of vacuum through 29 inches of vacuum while maintaining the temperature in the range of between 238° C. and 240° C. for a period between 1 to 4 hours.

9. The process of claim 1 wherein in step (e) the distillation is carried out at between 760 and 1–5 mm HG vacuum and at a temperature between about 230° C. and 240° C. for between 1 and 4 hours.

10. The process of claim 1 wherein the 2-hydroxyalkyl sulfonic acid salt is sodium isethionate and the fatty acids comprises EMERY® 626.

11. The process of claim 1 wherein said fatty acids are derived from coconut oil and are selected from the group consisting of C8–C18 coco fatty acids, C18 unsaturated coco fatty acids, coco fatty acids stripped to remove C8/C10 acids, hydrogenated coco fatty acids stripped to remove C8/C10 acids, hydrogenated coco fatty acids in the C8–C18 range, individual C12 through C18 fatty acids, where C18 is saturated or unsaturated, and any combination of C8 through C18 fatty acids or C18 unsaturated fatty acid.

12. The isethionate fatty acid ester formed by the process of claim 1.

13. The process of claim 1, wherein in step e, stripping is preferably carried out at a temperature in the range of 220° C. to 250° C.

14. The process of claim 1, wherein in step e, stripping is most preferably carried out at a temperature of about 240° C.

15. The process of claim 1 wherein step (a) is preferably carried out in the presence of an inert atmosphere at temperatures ranging between 220° C. to 250° C., the alkalinity of the sulfonic acid salt is preferably between 0.2 and 0.07 mgms KOH/gm, the acidity of the sulfonic acid salt is preferably less than 0.5 mgms KOH/gm, and the molar ratio of sulfonic acid salt to fatty acids is preferably 1:1.4.

16. The process of claim 1 wherein step (a) is most preferably carried out in the presence of an inert atmosphere at temperatures of about 240° C., the alkalinity of the sulfonic acid salt is most preferably less than 0.5 mgms KOH/gm, the acidity of the sulfonic acid salt is most preferably less than 0.2 mgms KOH/gm, and the molar ratio of sulfonic acid salt to fatty acids is most preferably 1:1.3.

17. The process of claim 1 wherein the molar ratio of sulfonic acid salt to fatty acids ranges from a maximum of 1:1.5 to a minimum of 1:1.25.

18. A non-catalyzed process of preparing sodium cocoyl isethionate which comprises the steps of:
(a) reacting sodium isethionate and coconut fatty acids at temperatures in the range of about 2000C. to 250° C., in the presence of an inert atmosphere, in the absence of sufficient acid or alkaline agents to catalyze the reaction, where the alkalinity of the sodium isethionate is not more than 1.5 mgms KOH/gm, and where the acidity of the sodium isethionate is not more than 1.0 mgms KOH/gm, the molar ratio of sodium isethionate to fatty acids ranging from a maximum of 1:1.5 to a minimum of 1:1.1;
(b) returning all distillate fatty acids to the reaction vessel;
(c) allowing the reaction to proceed substantially toward completion while maintaining said temperature and continuously removing water from the reaction mixture, until no further condensation can be achieved in the reaction vessel;
(d) discontinuing return of the distillate fatty acids and progressively reducing the pressure in the reaction vessel containing said reaction mass in the range of from 5 inches of vacuum through 29 inches of vacuum while maintaining the temperature in the range of between 238° C. and 240° C. for a period between 1 to 4 hours;
(e) distilling off free fatty acids from the reaction mass by stripping at a temperature in the range of 200° C. to 250° C.; and
(f) releasing the vacuum, discharging and flaking the sodium cocoyl isethionate so formed.

19. The process of claim 18 wherein said coconut fatty acid comprises from 8 to 24 carbon atoms and is selected from the group consisting of C8–C18 coco fatty acids, C18 unsaturated coco fatty acids, coco fatty acids stripped to remove C8/C10 acids, hydrogenated coco fatty acids stripped to remove C8/C10 acids, hydrogenated coco fatty acids in the C8–C18 range, individual C12 through C18 fatty acids, where C18 is saturated or unsaturated, and any combination of C8 through C18 fatty acids or C18 unsaturated fatty acid.

20. The process of claim 18 wherein in step (b) distillate fatty acids are returned to the reaction vessel in a ratio of 15 parts of distilled fatty acids to 85 parts of starting coconut fatty acids.

21. The process of claim 18 wherein the GAP or unknowns are lower than 5% of the total mass.

22. The process of claim 18 wherein the sodium cocoyl isethionate produced has an activity of at least 80%.

23. The process of claim 18 wherein there is no or negligible alteration in the molecular weight distribution of the sodium cocoyl isethionate produced as compared to the starting reactant coco fatty acids.

24. The process of claim 18 wherein in step (c) the reaction is allowed to proceed until the free fatty acid content of the reaction mass in the reaction vessel is in the range of 15 wt. % to 18 wt. %.

25. Sodium cocoyl isethionate produced by the process of claim 18 having a genuine molecular weight and a carbon chain distribution that is equal or substantially equal to that of the starting reactant coconut fatty acids.

26. Substantially soap-free sodium cocoyl isethionate produced by the process of claim 18.

27. SCI produced by the process of claim 18 having alkalinity in the range of 0.2 to 1.0.

28. The process of claim 18 wherein step (a) is preferably carried out in the presence of an inert atmosphere at temperatures ranging between 220° C. to 250° C., the alkalinity of the sulfonic acid salt is preferably between 0.2 and 0.07 mgms KOH/gm, the acidity of the sodium isethionate is preferably less than 0.5 mgms KOH/gm, and the molar ratio of sodium isethionate to fatty acids is preferably 1:1.4.

29. The process of claim 18 wherein step (a) is most preferably carried out in the presence of an inert atmosphere at temperatures of about 240° C., the alkalinity of the sodium isethionate is most preferably less than 0.5 mgms KOH/gm, the acidity of the sodium isethionate is most preferably less than 0.2 mgms KOH/gm, and the molar ratio of sodium isethionate to fatty acids is most preferably 1:1.3.

30. The process of claim 18 wherein the molar ratio of sulfonic acid salt to fatty acids ranges from a maximum of 1:1.5 to a minimum of 1:1.25.

31. The process of claim 18, wherein in step e, stripping is preferably carried out at a temperature in the range of 220° C. to 250° C.

32. The process of claim 18, wherein in step e, stripping is most preferably carried out at a temperature of about 240° C.

33. The process of claim 22 wherein the sodium cocoyl isethionate produced preferably has an activity between 83% and 88%.

34. The process of claim 22 wherein the sodium cocoyl isethionate produced most preferably has an activity over 85%.

35. Fatty acid esters of hydroxyalkyl sulfonate salts having the formula:

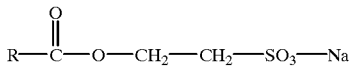

where R is cocoyl radical prepared by reacting fatty acids or a mixture of fatty acids with hydroxyalkyl sulfonate, wherein said fatty acid esters have a defined molecular weight equal to or substantially equal to the derived/theoretical molecular weight of the starting fatty acids and hydroxyalkyl sulfonate.

36. Sodium cocoyl isethionate having the following properties:

| | |
|---|---|
| appearance: | white to off-white flakes or chips or powder or noodles; |
| active content, %: | 80–90 |
| pH, 10% solution at 35° C.: | 4.0–6.0 |
| moisture, %: | 0.5 maximum |
| free fatty acid, %: | 7–16 |
| soap: | 0% |
| color, APHA, 5% in 30% n-propanol 70% distilled water | 50 maximum. |

* * * * *